United States Patent
Chen et al.

(10) Patent No.: US 10,071,991 B2
(45) Date of Patent: Sep. 11, 2018

(54) SUBSTITUTED PYRIDINE DERIVATIVES USEFUL AS C-FMS KINASE INHIBITORS

(71) Applicant: Janssen Pharmaceutica NV, Beerse (BE)

(72) Inventors: Jie Chen, Flemington, NJ (US); Matthew Donahue, Hattiesburg, MS (US); Heng-Keang Lim, Lawrenceville, NJ (US); Ronghui Lin, Ambler, PA (US); Rhys Salter, Doylestown, PA (US); Jiejun Wu, San Diego, CA (US); Yong Gong, Warrington, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/440,182

(22) Filed: Feb. 23, 2017

(65) Prior Publication Data

US 2017/0158678 A1    Jun. 8, 2017

Related U.S. Application Data

(62) Division of application No. 14/772,040, filed as application No. PCT/US2014/025308 on Mar. 13, 2014, now Pat. No. 9,611,259.

(60) Provisional application No. 61/791,007, filed on Mar. 15, 2013.

(51) Int. Cl.
   *C07D 405/14*    (2006.01)

(52) U.S. Cl.
   CPC ................ *C07D 405/14* (2013.01)

(58) Field of Classification Search
   CPC .................................... C07D 405/14
   USPC .................................... 546/275.1
   See application file for complete search history.

(56) References Cited

U.S. PATENT DOCUMENTS

2009/0105296 A1    4/2009    Illig et al.

FOREIGN PATENT DOCUMENTS

| CN | 101437514 A | 5/2009 |
|---|---|---|
| CN | 101889009 A | 11/2010 |
| JP | 2011501752 A | 1/2011 |

OTHER PUBLICATIONS

International Search Report from PCT/US2014/025308 dated Sep. 10, 2014.
Foster, A.B., "Deuterium isotope effects in studies of drug metabolism", TIPS (1984), vol. 5, pp. 524-527.

*Primary Examiner* — Patricia L Morris
(74) *Attorney, Agent, or Firm* — Baker & Hostetler LLP

(57) ABSTRACT

The present invention is directed to substituted pyridine derivatives, pharmaceutical compositions containing said derivatives and the use of said derivatives in the treatment of disorders mediated by c-fms kinase. The present invention is further directed to a process for the preparation of said substituted pyridine derivatives.

3 Claims, No Drawings

SUBSTITUTED PYRIDINE DERIVATIVES USEFUL AS C-FMS KINASE INHIBITORS

CROSS REFERENCE TO RELATED APPLICATIONS

This application is a divisional of U.S. patent application Ser. No. 14/772,040, filed Sep. 1, 2015; pending; which is a national stage of PCT Application No. PCT/US2014/025308, filed Mar. 13, 2014, which claims priority to U.S. Provisional Patent Application No. 61/791,007, filed Mar. 15, 2013. The entire disclosures of each of these patent applications are hereby incorporated in their entirety.

FIELD OF THE INVENTION

The present invention is directed to substituted pyridine derivatives, pharmaceutical compositions containing said derivatives and the use of said derivatives in the treatment of disorders mediated by c-fms kinase. The present invention is further directed to a process for the preparation of said substituted pyridine derivatives.

BACKGROUND OF THE INVENTION

Illig, C., et al., in US Patent Publication US2009/0105296 A1, published Apr. 23, 2009 disclosed c-fms kinase inhibitors of the following structural formula

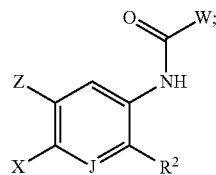

pharmaceutically acceptable salts thereof; and a process for their preparation.

SUMMARY OF THE INVENTION

The present invention is directed to compounds of formula (I)

(I)

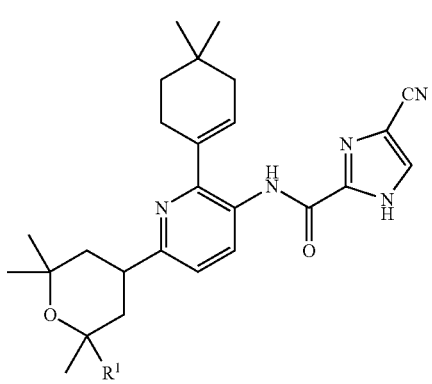

wherein $R^1$ is selected from the group consisting of —CH$_2$—OH and —C(O)OH; and enantiomers, diastereomers, racemates and pharmaceutically acceptable salts thereof.

In an embodiment, the present invention is directed to a compound of formula (I-M2)

(I-M2)

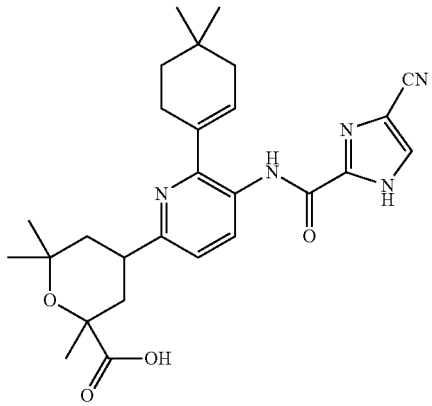

(also known as 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylic acid) and enantiomers, diastereomers, racemates and pharmaceutically acceptable salts thereof.

In another embodiment, the present invention is directed to a compound of formula (I-M7)

(I-M7)

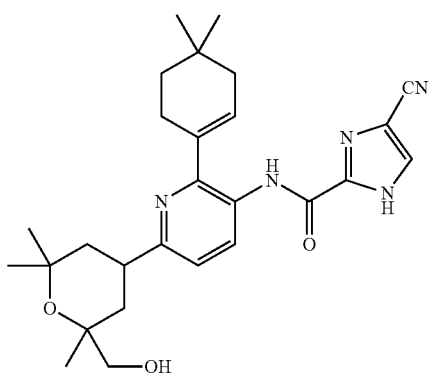

(also known as 4-cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1H-imidazole-2-carboxamide) and enantiomers, diastereomers, racemates and pharmaceutically acceptable salts thereof.

In additional embodiments, the compounds of formula (I) (i.e. the compound of formula (I-M2) and the compound of formula (I-M7)) are present in an isolated form. In additional embodiments, the compounds of formula (I) (i.e. the compound of formula (I-M2) and the compound of formula (I-M7)) are present in a substantially pure form. In additional embodiments, the compounds of formula (I) (i.e. the compound of formula (I-M2) and the compound of formula (I-M7)) are present in an isolated and substantially pure form.

The present invention is further directed to D4-deuterated compounds of formula (I), as described in more detail herein. In an embodiment, the present invention is directed to D4-deuterated compounds of formula (I-M2). In another embodiment, the present invention is directed to D4-deuterated compounds of formula (I-M7).

The present invention is further directed to D4-deuterated compounds of formula (P), as described in more detail herein.

The present invention is further directed to a process for the preparation of compounds of formula (I), as described in more detail herein. The present invention is further directed to a product prepared according to any of the processes described herein.

Illustrative of the invention is a pharmaceutical composition comprising a pharmaceutically acceptable carrier and a compound of formula (I). An illustration of the invention is a pharmaceutical composition made by mixing a compound of formula (I) and a pharmaceutically acceptable carrier. Illustrating the invention is a process for making a pharmaceutical composition comprising mixing a compound of formula (I) and a pharmaceutically acceptable carrier.

Exemplifying the invention are methods of treating a disorder mediated by c-fms kinase (selected from the group consisting of osteoporosis, Paget's disease, rheumatoid arthritis other forms of inflammatory arthritis, osteoarthritis, prosthesis failure, osteolytic sarcoma, myeloma, Hodgkin's lymphoma, tumor metastasis to bone, ovarian cancer, uterine cancer, breast cancer, prostate cancer, lung cancer, colon cancer, stomach cancer, hairy cell leukemia; metastasis from ovarian cancer, uterine cancer, breast cancer, prostate cancer, lung cancer, colon cancer, stomach cancer, or hairy cell leukemia; glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia, Alzheimer's dementia; pain, skeletal pain caused by tumor metastasis or osteoarthritis, visceral pain, inflammatory pain, neurogenic pain; an autoimmune disease, systemic lupus erythematosus, rheumatoid arthritis, other forms of inflammatory arthritis, psoriasis, Sjogren's syndrome, multiple sclerosis and uveitis; preferably rheumatoid arthritis) comprising administering to a subject in need thereof a therapeutically effective amount of a compound of formula (I), or a pharmaceutical composition comprising a compound of formula (I), as herein described.

In another embodiment, the present invention is directed to a compound of formula (I) for use in the treatment of a disorder selected from the group consisting of osteoporosis, Paget's disease, rheumatoid arthritis other forms of inflammatory arthritis, osteoarthritis, prosthesis failure, osteolytic sarcoma, myeloma, Hodgkin's lymphoma, tumor metastasis to bone, ovarian cancer, uterine cancer, breast cancer, prostate cancer, lung cancer, colon cancer, stomach cancer, hairy cell leukemia; metastasis from ovarian cancer, uterine cancer, breast cancer, prostate cancer, lung cancer, colon cancer, stomach cancer, or hairy cell leukemia; glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia, Alzheimer's dementia; pain, skeletal pain caused by tumor metastasis or osteoarthritis, visceral pain, inflammatory pain, neurogenic pain; an autoimmune disease, systemic lupus erythematosus, rheumatoid arthritis, other forms of inflammatory arthritis, psoriasis, Sjogren's syndrome, multiple sclerosis and uveitis. Preferably, the disorder mediated by c-fms kinase is rheumatoid arthritis.

Another example of the invention is the use of a compound of formula (I) in the preparation of a medicament for treating: (a) osteoporosis, (b) Paget's disease, (c) rheumatoid arthritis, (d) other forms of inflammatory arthritis, (e) osteoarthritis, (f) prosthesis failure, (g) osteolytic sarcoma, (h) myeloma, (i) Hodgkin's lymphoma, (j) tumor metastasis to bone, (k) ovarian cancer, (l) uterine cancer, (m) breast cancer, (n) prostate cancer, (o) lung cancer, (p) colon cancer, (q) stomach cancer, (r) hairy cell leukemia; (s) metastasis from ovarian cancer, uterine cancer, breast cancer, prostate cancer, lung cancer, colon cancer, stomach cancer, or hairy cell leukemia; (t) glomerulonephritis, (u) inflammatory bowel disease, (v) sarcoidosis, (w) congestive obstructive pulmonary disease, (x) idiopathic pulmonary fibrosis, (y) asthma, (z) pancreatitis, (aa) HIV infection, (ab) psoriasis, (ac) diabetes, (ad) tumor related angiogenesis, (ae) age-related macular degeneration, (af) diabetic retinopathy, (ag) restenosis, (ah) schizophrenia, (ai) Alzheimer's dementia; (aj) pain, (ak) skeletal pain caused by tumor metastasis or osteoarthritis, (al) visceral pain, (am) inflammatory pain, (an) neurogenic pain; (ao) an autoimmune disease, (ap) systemic lupus erythematosus, (aq) rheumatoid arthritis, (ar) other forms of inflammatory arthritis, (as) psoriasis, (at) Sjogren's syndrome, (au) multiple sclerosis and (av) uveitis; in a subject in need thereof.

In another example, the present invention is directed to a compound of formula (I) for use in a methods for treating a disorder mediated by c-fms kinase (selected from the group consisting of osteoporosis, Paget's disease, rheumatoid arthritis other forms of inflammatory arthritis, osteoarthritis, prosthesis failure, osteolytic sarcoma, myeloma, Hodgkin's lymphoma, tumor metastasis to bone, ovarian cancer, uterine cancer, breast cancer, prostate cancer, lung cancer, colon cancer, stomach cancer, hairy cell leukemia; metastasis from ovarian cancer, uterine cancer, breast cancer, prostate cancer, lung cancer, colon cancer, stomach cancer, or hairy cell leukemia; glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia, Alzheimer's dementia; pain, skeletal pain caused by tumor metastasis or osteoarthritis, visceral pain, inflammatory pain, neurogenic pain; an autoimmune disease, systemic lupus erythematosus, rheumatoid arthritis, other forms of inflammatory arthritis, psoriasis, Sjogren's syndrome, multiple sclerosis and uveitis), in a subject in need thereof.

In another embodiment, the present invention is directed to a compound of formula (I) for the treatment of a disorder mediated by c-fms kinase (selected from the group consisting of osteoporosis, Paget's disease, rheumatoid arthritis other forms of inflammatory arthritis, osteoarthritis, prosthesis failure, osteolytic sarcoma, myeloma, Hodgkin's lymphoma, tumor metastasis to bone, ovarian cancer, uterine cancer, breast cancer, prostate cancer, lung cancer, colon cancer, stomach cancer, hairy cell leukemia; metastasis from ovarian cancer, uterine cancer, breast cancer, prostate cancer, lung cancer, colon cancer, stomach cancer, or hairy cell leukemia; glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia, Alzheimer's dementia; pain, skeletal pain caused by tumor metastasis or osteoarthritis, visceral pain, inflammatory pain, neurogenic pain; an autoimmune disease, systemic lupus erythematosus, rheumatoid arthritis, other forms of inflammatory arthritis, psoriasis, Sjogren's syndrome, multiple sclerosis and uveitis; preferably rheumatoid arthritis).

DETAILED DESCRIPTION OF THE INVENTION

The present invention is directed to compounds of formula (I)

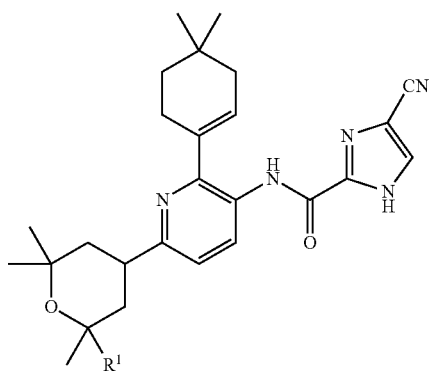

(I)

wherein $R^1$ is as herein defined; and enantiomers, diastereomers, racemates and pharmaceutically acceptable salts thereof; useful as active metabolites of the compound of formula (P)

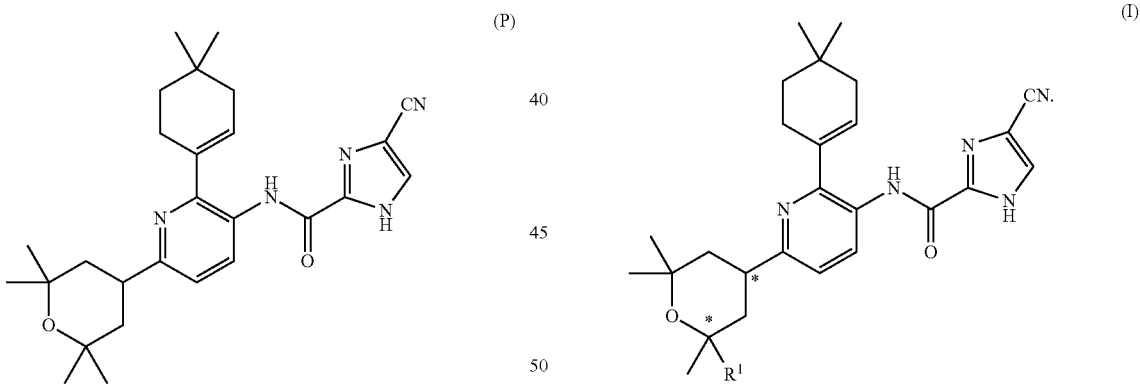

also known as 4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamide (as disclosed in Illig, C., et al., in US Patent Publication US2009/0105296 A1, published Apr. 23, 2009).

The compound of formula (P) is useful as a protein tyrosine kinase inhibitors, more particularly as an inhibitor of c-fms kinase. As disclosed in Illig, C., et al., US Patent Publication US2009/0105296 A1, the c-fms kinase inhibitor of formula (P) is useful for the treatment of diseases including, but not limited to: osteoporosis, Paget's disease, rheumatoid arthritis, other forms of inflammatory arthritis, osteoarthritis, prosthesis failure, osteolytic sarcoma, myeloma, tumor metastasis to bone, ovarian cancer, uterine cancer, breast cancer, prostate cancer, lung cancer, colon cancer, stomach cancer, hairy cell leukemia; metastasis from ovarian cancer, uterine cancer, breast cancer, prostate cancer, lung cancer, colon cancer, stomach cancer, or hairy cell leukemia; glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia, Alzheimer's dementia; pain, skeletal pain caused by tumor metastasis or osteoarthritis, visceral pain, inflammatory pain, neurogenic pain; an autoimmune disease, systemic lupus erythematosus, rheumatoid arthritis, other forms of inflammatory arthritis, psoriasis, Sjogren's syndrome, multiple sclerosis and uveitis.

The compounds of formula (I) (i.e. the compound of formula (I-M2) and the compound of formula (I-M7)) are active metabolites of the compound of formula (P). The compounds of formula (I) were initially identified from LC-MS analysis of human plasma samples collected during a first-in-human clinical trial with multiple ascending dosing of the compound of formula (P).

In an embodiment of the present invention, $R^1$ is —CH$_2$—OH. In another embodiment of the present invention, $R^1$ is —C(O)—OH.

One skilled in the art will recognize that the compounds of formula (I) contain two stereo-centers, located at the bonds designated with a "*" in the following structural representation:

(I)

The present invention includes individual, isolated and/or substantially pure enantiomers and/or diastereomers, as well as racemates, and mixtures of said enantiomers and/or diastereomers. In an embodiment, the diastereomeric excess of a stereo-isomer of the compound of formula (I) (including any D4-deuterated stereo-isomer of the compound of formula (I)) is greater than or equal to about 80%, preferably greater than or equal to about 90%, more preferably, greater than or equal to about 95%, more preferably, greater than or equal to about 98%, more preferably, greater than or equal to about 99%.

In an embodiment, the present invention is directed to an isolated or substantially pure compound of formula (I-M2-2R,4R)

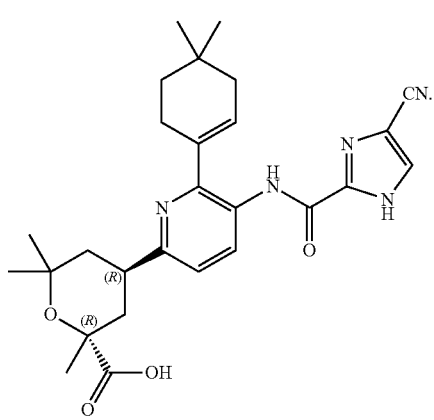

(I-M2-2R, 4R)

In an embodiment, the present invention is directed to an isolated or substantially pure compound of formula (I-M2-2R,4S)

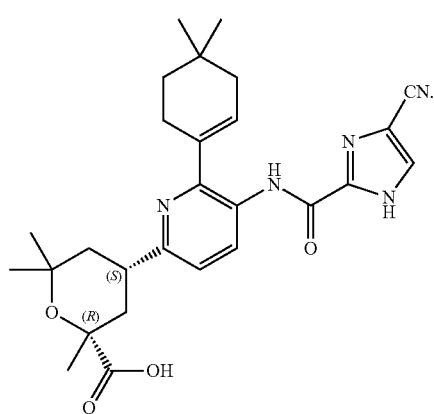

(I-M2-2R, 4S)

In an embodiment, the present invention is directed to an isolated or substantially pure compound of formula (I-M2-2S,4S)

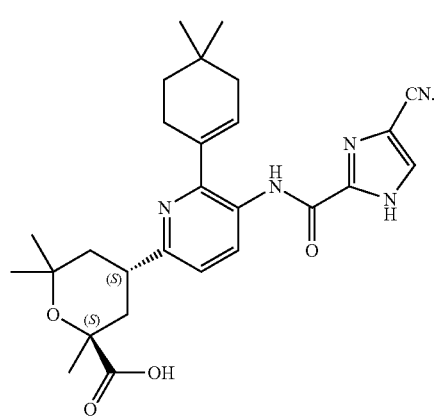

(I-M2-2S, 4S)

In an embodiment, the present invention is directed to an isolated or substantially pure compound of formula (I-M2-2S,4R)

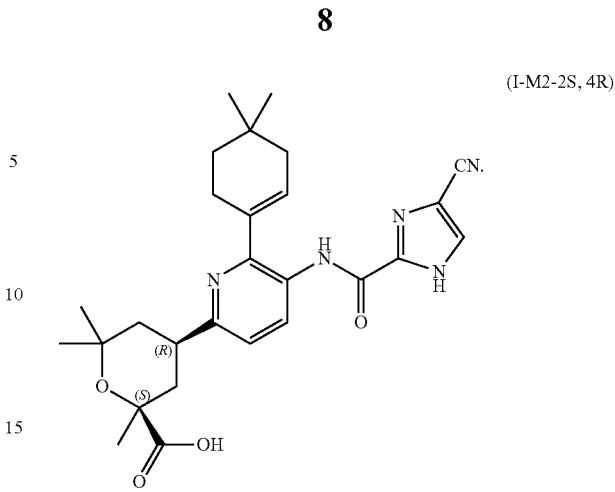

(I-M2-2S, 4R)

In an embodiment, the present invention is directed to a racemic mixture of the compound of formula (I-M2-2R,4S) and the compound of formula (I-M2-2S,4R).

In a another embodiment, the present invention is directed to an isolated or substantially pure diastereomer of the compound (I-M2) selected from the group consisting of the compound of formula (I-M2-2R,4S) and the compound of formula (I-M2-2S,4R).

In an embodiment, the present invention is directed to an isolated or substantially pure compound of formula (I-M7-2R,4R)

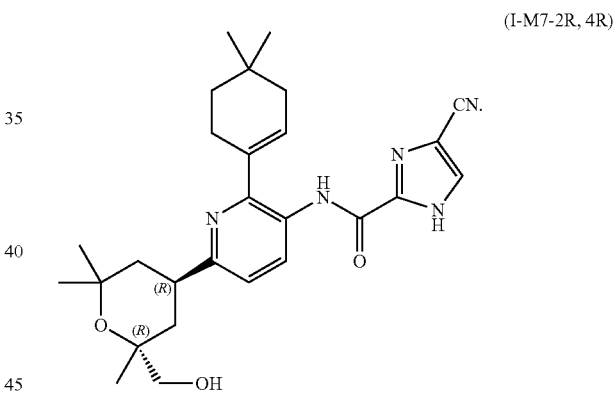

(I-M7-2R, 4R)

In an embodiment, the present invention is directed to an isolated or substantially pure compound of formula (I-M7-2R,4S)

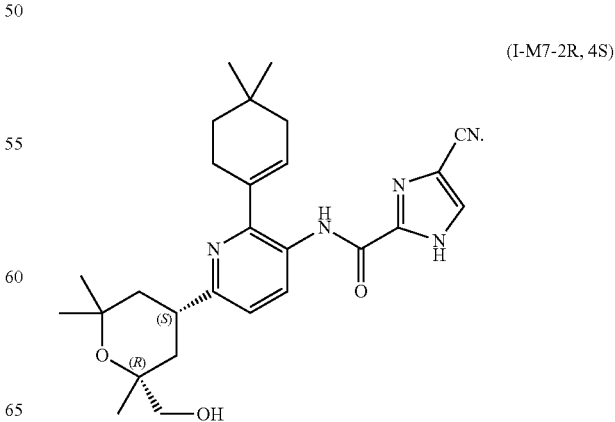

(I-M7-2R, 4S)

In an embodiment, the present invention is directed to an isolated or substantially pure compound of formula (I-M7-2S,4S)

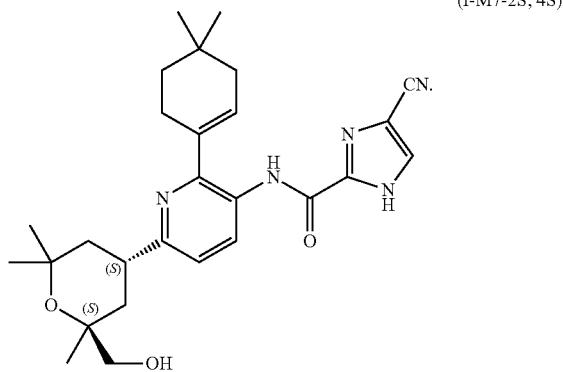

(I-M7-2S, 4S)

In an embodiment, the present invention is directed to an isolated or substantially pure compound of formula (I-M7-2S,4R)

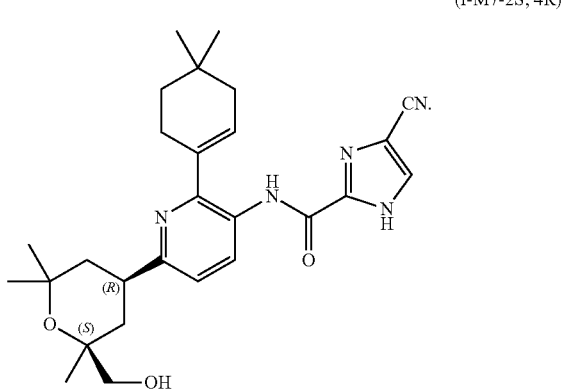

(I-M7-2S, 4R)

In an embodiment, the present invention is directed to a racemic mixture of the compound of formula (I-M7-2R,4S) and the compound of formula (I-M7-2S,4R).

In a another embodiment, the present invention is directed to an isolated or substantially pure diastereomer of the compound (I-M7) selected from the group consisting of the compound of formula (I-M7-2R,4S) and the compound of formula (I-M7-2S,4R).

One skilled in the art will recognize that the (2R,4R)- and the (2S,4S)-diastereomers of the compound of formula (I-M2) and the compound of formula (I-M7) are sterically hindered (present in more of a "cis-type" stereo-orientation), whereas the (2R,4S)- and the (2S,4R)-diastereomers of the compound of formula (I-M2) and the compound of formula (I-M7) are less sterically hindered (present in more of a "trans-type" stereo-orientation).

It is theorized that in the synthesis of the compound of formula (I-M2) and the synthesis of the compound of formula (I-M7), as herein described, the sterically hindered (2S,4S)- and (2R,4R)-diastereomers are prepared in relatively small amounts. It is further theorized that said (2S, 4S)- and (2R,4R)-diastereomers are substantially removed from the final product mixture in the work-up and/or purification steps.

It is intended that within the scope of the present invention, any element, in particular when mentioned in relation to a compound of formula (I), shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon, oxygen and/or nitrogen include within their scope respectively $^{12}C$, $^{13}C$ and $^{14}C$; $^{16}O$ and $^{18}O$; $^{14}N$ and $^{15}N$. The isotopes may be radioactive or non-radioactive. Radiolabelled compounds of formula (I) may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

The present invention is further directed to $D_4$-deuterated compounds of formula (I). In an embodiment, the present invention is directed to $D_4$-deuterated compounds of formula (I-M2), more particularly, (I-M2-D4a) and (I-M2-D4b)

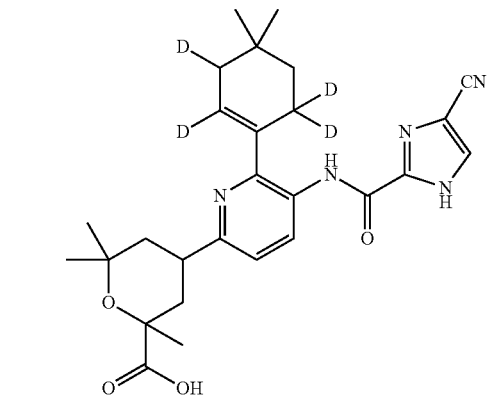

(I-M2-D4a)

and

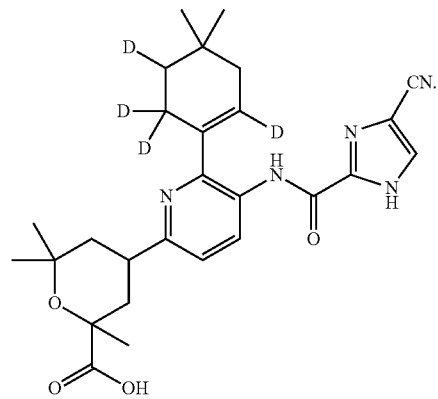

(I-M2-D4b)

In another embodiment, the present invention is directed to $D_4$-deuterated compounds of formula (I-M7), more particularly, (I-M7-D4a) and (I-M7-D4b)

(I-M7-D4a)

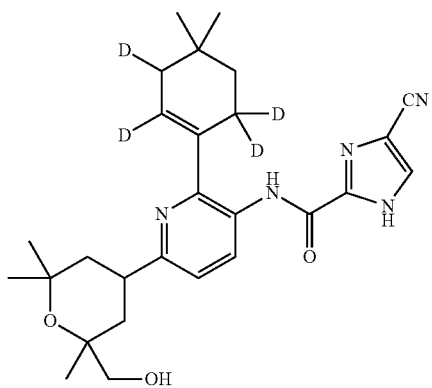

(I-M7-D4b)

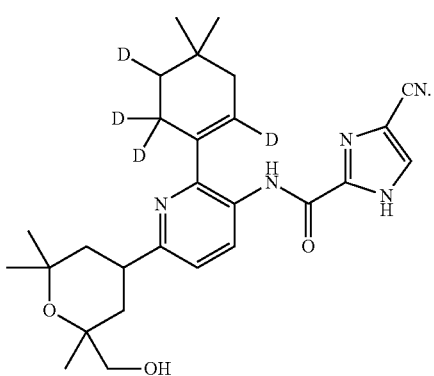

The present invention is further directed to a $D_4$-deuterated compound of formula (P). In an embodiment, the present invention is directed to a mixture of 2',3',6',6'-[$D_4$]-deuterated and 2',5',6',6'-[$D_4$]-deuterated compounds of formula (P), more particularly, a mixture of a compound of formula (P-D4a)

(P-D4a)

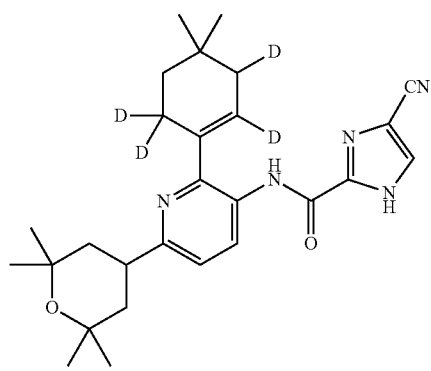

and a compound of formula (P-D4b)

(P-D4b)

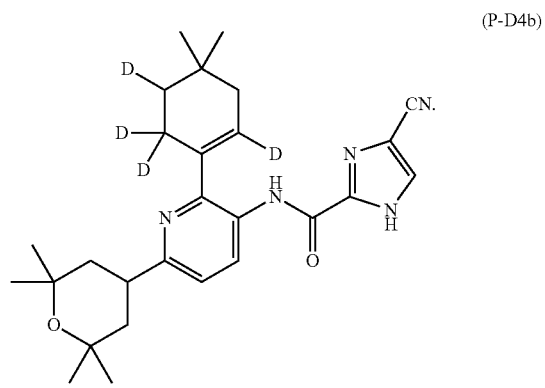 [SMILES: [2H]C1=C(c2nc(C3CC(C)(C)OC(C)(C)C3)ccc2NC(=O)c2nc(C#N)c[nH]2)C([2H])([2H])C([2H])C(C)(C)C1]

In another embodiment, the compound of formula (P-D4a) and the compound of formula (P-D4b) are present in mixture at a molar ratio of about 1:1.

As used herein, unless otherwise noted, the term "isolated form" shall mean that the compound is present in a form which is separate from any biological environment (e.g. plasma, blood, gastric fluids, urine, cerebrospinal fluid, and the like). In an embodiment of the present invention, the compound of formula (I) is present in an isolated form. In another embodiment of the present invention, the compound of formula (I-M2) is present in an isolated form. In another embodiment of the present invention, the compound of formula (I-M7) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is a substantially pure form. In another embodiment of the present invention, the compound of formula (I-M2) is a substantially pure form. In another embodiment of the present invention, the compound of formula (I-M7) is a substantially pure form.

As used herein, unless otherwise noted, the term "substantially pure as measured by HPLC" shall mean that the calculated area under the curve for the compound of formula (I), as measured by UV HPLC analysis is greater than about 90%, preferably, the greater than about 95%, more preferably, greater than about 98%, more preferably still, greater than about 99%. In an embodiment of the present invention, the compound of formula (I) is a substantially pure form as measured by HPLC. In another embodiment of the present invention, the compound of formula (I-M2) is a substantially pure form as measured by HPLC. In another embodiment of the present invention, the compound of formula (I-M7) is a substantially pure form as measured by HPLC.

As used herein, unless otherwise noted, the term "substantially free of corresponding salt form(s)" when used to described the compound of formula (I) shall mean that mole percent of salt forms of the compound of formula (I) is less than about 5 mole percent, preferably less than about 2 mole percent, more preferably, less than about 0.5 mole percent, most preferably less than about 0.1 mole percent. In an embodiment of the present invention, the compound of formula (I) is substantially free of corresponding salt form(s). In another embodiment of the present invention, the compound of formula (I-M2) is substantially free of corresponding salt form(s). In another embodiment of the present invention, the compound of formula (I-M7) is substantially free of corresponding salt form(s).

Where the compound according to this invention has at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%.

Unless otherwise noted, where a stereogenic center is present, the S- and R-designations have been arbitrarily assigned, since the exact stereo-configuration of the center(s) has not been determined. As such, the use of the S- and R-designations is not intended to define the absolute optical rotation of the designated bond.

The compounds of formula (I) are inhibitors of protein tyrosine kinases, such as c-fms, useful in the prevention and treatment of disorders resulting from actions of these kinases.

In certain embodiments, the present invention is directed to methods of inhibiting a protein tyrosine kinase comprising contacting the protein tyrosine kinase with therapeutically effective amount of a compound of formula (I). A preferred tyrosine kinase is c-fms.

In various embodiments of the present invention, the protein tyrosine kinases inhibited by the compound of formula (I) are located in cells, in a mammal or in vitro. In the case of mammals, which includes humans, preferably, a therapeutically effective amount of a pharmaceutically acceptable form of a compound of formula (I) is administered.

The present invention further provides methods of treating cancer in mammals, including humans, comprising administration of a therapeutically effective amount of a compound of formula (I), preferably a pharmaceutically acceptable composition comprising a compound of formula (I). Exemplary cancers include, but are not limited to, acute myeloid leukemia, acute lymphocytic leukemia, Hodgkins lymphoma, ovarian cancer, uterine cancer, prostate cancer, lung cancer, breast cancer, colon cancer, stomach cancer, and hairy cell leukemia. The present invention also provides methods of treating certain precancerous lesions including myelofibrosis. In another embodiment of the present invention, an effective amount of at least one compound of formula (I) is administered in combination with an effective amount of a chemotherapeutic agent.

The present invention further provides methods of treating and/or preventing metastasis arising from cancers that include, but are not limited to, Hodgkins lymphoma, ovarian cancer, uterine cancer, prostate cancer, lung cancer, breast cancer, colon cancer, stomach cancer, and hairy cell leukemia, comprising administration of a therapeutically effective amount of a compound of formula (I), preferably a pharmaceutically acceptable composition comprising a compound of formula (I).

The present invention further provides methods of treating osteoporosis, Paget's disease, and other diseases in which bone resorption mediates morbidity including rheumatoid arthritis and other forms of inflammatory arthritis, osteoarthritis, prosthesis failure, osteolytic sarcoma, myeloma, and tumor metastasis to bone as occurs frequently in cancers including, but not limited to, breast cancer, prostate cancer, and colon cancer, comprising administration of a therapeutically effective amount of a compound of formula (I), preferably a pharmaceutically acceptable composition comprising a compound of formula (I).

The present invention also provides methods of treating pain, in particular skeletal pain caused by tumor metastasis or osteoarthritis, as well as visceral, inflammatory, and neurogenic pain, comprising administration of a therapeutically effective amount of a compound of formula (I), preferably a pharmaceutically acceptable composition comprising a compound of formula (I).

The present invention also provides methods of treating cardiovascular, inflammatory, and autoimmune diseases in mammals, including humans, comprising administration of a therapeutically effective amount of a compound of formula (I), preferably a pharmaceutically acceptable composition comprising a compound of formula (I). Examples of diseases with an inflammatory component include glomerulonephritis, inflammatory bowel disease, prosthesis failure, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia or Alzheimer's dementia. Other diseases that may be effectively treated with a compound of formula (I) include, but are not limited to atherosclerosis and cardiac hypertrophy.

The present invention is further directed to methods of treating autoimmune diseases such as systemic lupus erythematosus, rheumatoid arthritis, and other forms of inflammatory arthritis, psoriasis, Sjogren's syndrome, multiple sclerosis, or uveitis, comprising administration of a therapeutically effective amount of a compound of formula (I), preferably a pharmaceutically acceptable composition comprising a compound of formula (I).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

One skilled in the art will recognize that, where not otherwise specified, the reaction step(s) is performed under suitable conditions, according to known methods, to provide the desired product. One skilled in the art will further recognize that wherein a reaction step of the present invention may be carried out in a variety of solvents or solvent systems, said reaction step may also be carried out in a mixture of the suitable solvents or solvent systems.

One skilled in the art will recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Abbreviations used in the specification, particularly the Schemes and Examples, are as follows:
ATP=Adenosine triphosphate
Brij-35=(Polyoxyethyleneglycol dodecyl ether) (detergent)
DCE=1,1-Dichloroethane
DCM=Dichloromethane
DIBAL=Diisobutyl aluminum hydride
DIPEA=Diisopropylethylamine
DME=Dimethoxyethane
DMF=Dimethylformamide
DMSO=Dimethylsulfoxide
DTT=Dithiothreitol
EDCI=1-Ethyl-3-(3-dimethylaminopropyl) carbodiimide
EDTA=Ethylene Diamine Tetraacetic Acid
$Et_3N$=Triethylamine
EtOH=Ethanol
HEPES=4-(2-Hydroxyethyl)-1-Piperizine Ethane Sulfonic Acid
HOAc=Acetic acid
KHMDS=Potassium bis(trimethylsilyl)amide
KOAc=Potassium Acetate
LDA=Lithium diisopropylamide
LiHMDS=Lithium bis(trimethylsilyl)amide
MeOH=Methanol
MOPS=3-(N-morpholino)propanesulfonic acid
n-Bu=n-Butyl
NBS=N-Bromosuccinimide
OTf=Triflate (i.e $—O—SO_2—CF_3$)
PCC=Pyridinium chlorochromate
$Pd(dba)_2Cl_2$=Bis(dibenzylideneacetone)palladium(II) dichloride
$Pd(dppf)_2Cl_2$=[1,1'-Bis(diphenylphosphino)ferrocene]dichloropalladium(II), complex
$Pd(PPh_3)_2Cl_2$=Bis(triphenylphosphine) palladium (II) dichloride
$PhN(Tf)_2$ or $Tf_2NPh$=Phenyl bis((trifluoromethyl)sulfonyl) amine
PPTS=Pyridinium p-toluenesulfonate
PyBrop=Bromo-tris-pyrrolidino-phosphonium hexafluorophosphate
RFU=Relative fluorescence units
SEM=2-(Trimethylsilyl)ethoxymethyl-
TBAF=Tetrabutyl ammonium fluoride
TEA=Triethylamine
$Tf_2O$=Triflic anhydride or Trifluoromethanesulfonic anhydride
THF=Tetrahydrofuran
TFA=Trifluoroacetic acid General Synthetic Schemes Compounds of formula (I) may be prepared from a common intermediate, n-butyl 4-(5-(4-cyano-1-((2-(trimethylsilyl)ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylate, which may be prepared as described in Scheme 1, below.

Scheme 1

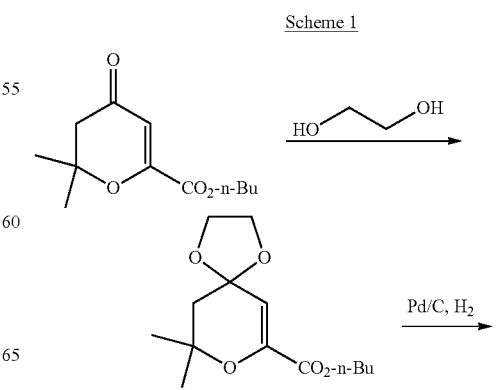

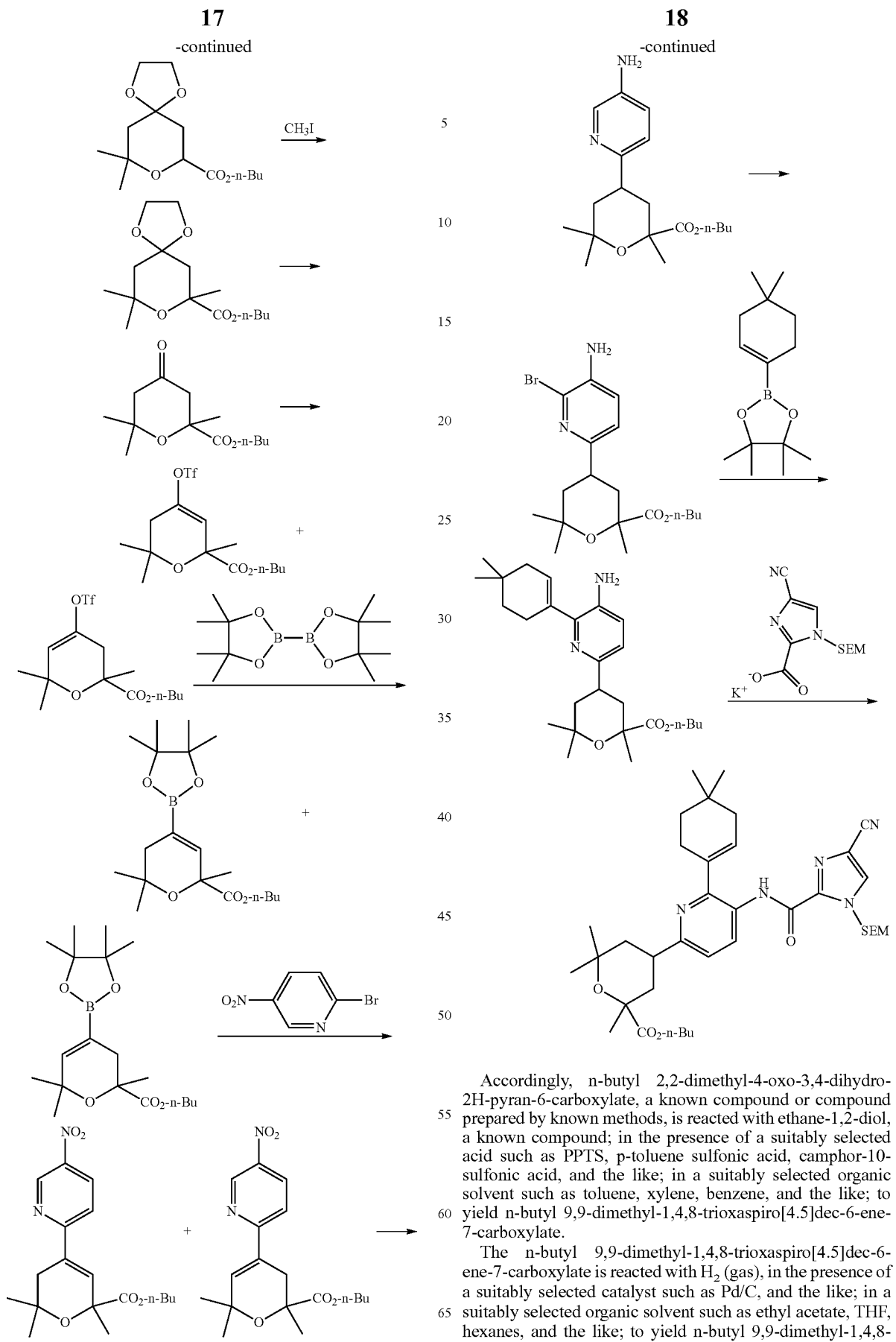

Accordingly, n-butyl 2,2-dimethyl-4-oxo-3,4-dihydro-2H-pyran-6-carboxylate, a known compound or compound prepared by known methods, is reacted with ethane-1,2-diol, a known compound; in the presence of a suitably selected acid such as PPTS, p-toluene sulfonic acid, camphor-10-sulfonic acid, and the like; in a suitably selected organic solvent such as toluene, xylene, benzene, and the like; to yield n-butyl 9,9-dimethyl-1,4,8-trioxaspiro[4.5]dec-6-ene-7-carboxylate.

The n-butyl 9,9-dimethyl-1,4,8-trioxaspiro[4.5]dec-6-ene-7-carboxylate is reacted with $H_2$ (gas), in the presence of a suitably selected catalyst such as Pd/C, and the like; in a suitably selected organic solvent such as ethyl acetate, THF, hexanes, and the like; to yield n-butyl 9,9-dimethyl-1,4,8-trioxaspiro[4.5]decane-7-carboxylate.

The n-butyl 9,9-dimethyl-1,4,8-trioxaspiro[4.5]decane-7-carboxylate is reacted with CH$_3$I, a known compound; in the presence of a suitably selected base such as LDA, LiHMDS, KHMDS, and the like; in a suitably selected organic solvent such as THF, 1,4-dioxane, DME, and the like; at a temperature of about −78° C.; to yield n-butyl 7,9,9-trimethyl-1,4,8-trioxaspiro[4.5]decane-7-carboxylate.

The n-butyl 7,9,9-trimethyl-1,4,8-trioxaspiro[4.5]decane-7-carboxylate is reacted with a suitably selected acid such as HCl, HBr, H$_3$PO$_4$, and the like; in a suitably selected reagent and organic solvent such as acetone, 2-butanone, cyclopentanone, and the like to yield n-butyl 2,6,6-trimethyl-4-oxotetrahydro-2H-pyran-2-carboxylate.

The n-butyl 2,6,6-trimethyl-4-oxotetrahydro-2H-pyran-2-carboxylate is reacted with a suitably selected source of triflate such as PhN(Tf)$_2$, Tf$_2$O, and the like; upon the treatment of a suitably selected base such as LDA, LiHMDS, KHMDS, and the like; in a suitably selected organic solvent such as THF, 1,4-dioxane, DME, and the like; at a temperature of about −78° C.; to yield a mixture of n-butyl 2,6,6-trimethyl-4-(((trifluoromethyl)sulfonyl)oxy)-5,6-dihydro-2H-pyran-2-carboxylate and n-butyl 2,6,6-trimethyl-4-(((trifluoromethyl)sulfonyl)oxy)-3,6-dihydro-2H-pyran-2-carboxylate.

The mixture of n-butyl 2,6,6-trimethyl-4-(((trifluoromethyl)sulfonyl)oxy)-5,6-dihydro-2H-pyran-2-carboxylate and n-butyl 2,6,6-trimethyl-4-(((trifluoromethyl)sulfonyl)oxy)-3,6-dihydro-2H-pyran-2-carboxylate is reacted with bis(pinacolato)diboron, a known compound; in the presence of a suitably selected palladium coupling agent such as Pd(dppf)$_2$Cl$_2$, Pd(dba)$_2$Cl$_2$, Pd(PPh$_3$)$_2$Cl$_2$, and the like; in the presence of a suitably selected inorganic base such as KOAc, Na$_2$CO$_4$, Cs$_2$CO$_3$, and the like; in a suitably selected organic solvent such as 1,4-dioxane, DME, THF, and the like; at a temperature in the range of from about 15° C. to about 120° C., for example, at about 100° C.; to yield a mixture of n-butyl 2,6,6-trimethyl-4-(4,4,5,5-tetramethyl-1,3,2-dioxaborolan-2-yl)-5,6-dihydro-2H-pyran-2-carboxylate and n-butyl 2,6,6-trimethyl-4-(4,4,5,5-tetramethyl-1,3,2-dioxaborolan-2-yl)-3,6-dihydro-2H-pyran-2-carboxylate.

The mixture of n-butyl 2,6,6-trimethyl-4-(4,4,5,5-tetramethyl-1,3,2-dioxaborolan-2-yl)-5,6-dihydro-2H-pyran-2-carboxylate and n-butyl 2,6,6-trimethyl-4-(4,4,5,5-tetramethyl-1,3,2-dioxaborolan-2-yl)-3,6-dihydro-2H-pyran-2-carboxylate is reacted with 2-bromo-5-nitropyridine, a known compound; in the presence of a suitably selected palladium coupling agent such as Pd(dppf)$_2$Cl$_2$, Pd(dpa)$_2$Cl$_2$, Pd(PPh$_3$)$_2$Cl$_2$, and the like; in the presence of a suitably selected inorganic base such as Na$_2$CO$_3$, K$_2$CO$_3$, Cs$_2$CO$_3$, and the like; in a suitably selected organic solvent or mixture of organic solvents, for example in a mixture of DME, ethanol and water; at a temperature in the range of from about 15° C. to about 120° C., for example at about 120° C., heated via microwave; to yield a mixture of n-butyl 2,6,6-trimethyl-4-(5-nitropyridin-2-yl)-5,6-dihydro-2H-pyran-2-carboxylate and n-butyl 2,6,6-trimethyl-4-(5-nitropyridin-2-yl)-5,6-dihydro-2H-pyran-2-carboxylate.

The mixture of n-butyl 2,6,6-trimethyl-4-(5-nitropyridin-2-yl)-5,6-dihydro-2H-pyran-2-carboxylate and n-butyl 2,6,6-trimethyl-4-(5-nitropyridin-2-yl)-5,6-dihydro-2H-pyran-2-carboxylate is reacted with H$_2$ (gas); in the presence of a suitably selected catalyst or mixture of catalysts, such as Pd/C, PtO$_2$, and the like; in a suitably selected organic solvent such as ethyl acetate, THF, 1,4-dioxane, and the like; to yield n-butyl 4-(5-aminopyridin-2-yl)-2,6,6-trimethyltetrahydro-2H-pyran-2-carboxylate.

The n-butyl 4-(5-aminopyridin-2-yl)-2,6,6-trimethyltetrahydro-2H-pyran-2-carboxylate is reacted with a suitably selected source of bromine, such as NBS, Br$_2$, BrCl, and the like; in a suitably selected organic solvent such as acetonitrile, DCM, DMF, and the like; at a temperature in the range of from about −5° C. to about 60° C., for example at about 0° C.; to yield n-butyl 4-(5-amino-6-bromopyridin-2-yl)-2,6,6-trimethyltetrahydro-2H-pyran-2-carboxylate.

One skilled in the art will recognize that upon completion of the reaction (for example, when chromatography analysis indicated consumption of the starting material) any remaining brominating agent is preferably quenched with a 10% aqueous solution of sodium thiosulfate.

The n-butyl 4-(5-amino-6-bromopyridin-2-yl)-2,6,6-trimethyltetrahydro-2H-pyran-2-carboxylate is reacted with 2-(4,4-dimethylcyclohex-1-en-1-yl)-4,4,5,5-tetramethyl-1,3,2-dioxaborolane, a known compound; in the presence of a suitably selected coupling agent such as Pd(PPh$_3$)$_2$Cl$_2$, Pd(dba)$_2$Cl$_2$, Pd(PPh$_3$)$_2$Cl$_2$, and the like; in the presence of a suitably selected inorganic base such as Na$_2$CO$_3$, K$_2$CO$_3$, Cs$_2$CO$_3$, and the like; in a suitably selected solvent or mixture of solvents such as a mixture of 1,4-dioxane and water, THF, DME, and the like; to yield n-butyl 4-(5-amino-6-(4,4-dimethylcyclohex-1-en-1-yl)pyridin-2-yl)-2,6,6-trimethyltetrahydro-2H-pyran-2-carboxylate.

The n-butyl 4-(5-amino-6-(4,4-dimethylcyclohex-1-en-1-yl)pyridin-2-yl)-2,6,6-trimethyltetrahydro-2H-pyran-2-carboxylate is reacted with potassium 4-cyano-1-((2-(trimethylsilyl)ethoxy)methyl)-1H-imidazole-2-carboxylate, a known compound; in the presence of a suitably selected coupling reagent such as PyBrop, DCC, EDCI, and the like; in the presence of a suitably selected organic base such as DIPEA, TEA, pyridine, and the like; in a suitably selected organic solvent such as DCM, DCE, THF, and the like; to yield n-butyl 4-(5-(4-cyano-1-((2-(trimethylsilyl)ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylate.

The compound of formula (I-M2) may be prepared as described in more detail in Scheme 2, below.

Scheme 2

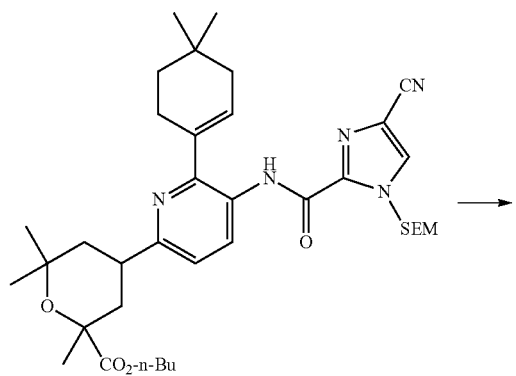

-continued

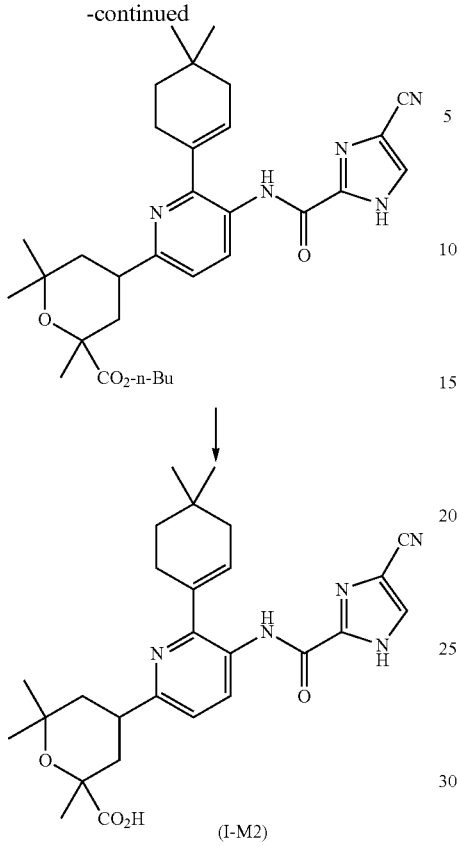

(I-M2)

Scheme 3

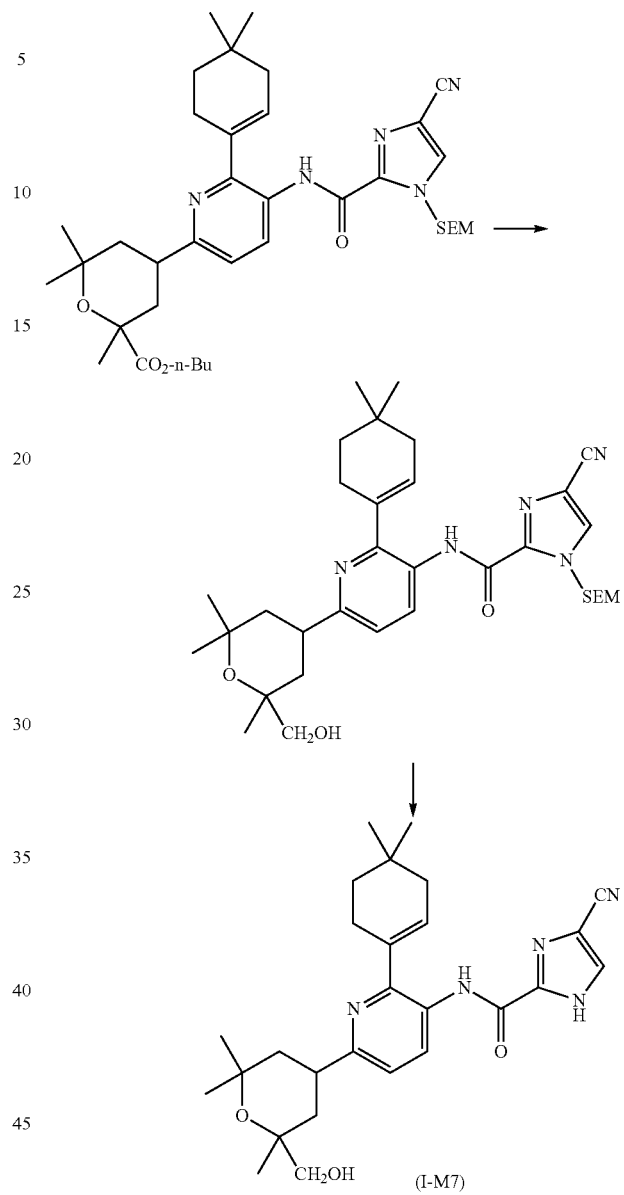

(I-M7)

Accordingly, n-butyl 4-(5-(4-cyano-1-((2-(trimethylsilyl) ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylate, prepared for example as described in Scheme 1 above, is reacted to remove the SEM protecting group, reacting with a suitably selected desilylating reagent such as TBAF, KF, pyridinium hydrofluoride, and the like; in a suitably selected organic solvent such as THF, 1,4-dioxane, diethyl ether, and the like; at a temperature in the range of from about 0° C. to about 120° C., for example at about 60-65° C., heated by microwave; to yield n-butyl 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylate.

The n-butyl 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylate is reacted with a suitably selected acid or base such as LiOH, NaOH, KOH, and the like; in a suitably selected solvent such as water, MeOH, EtOH, and the like; to yield the 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylic acid, or its corresponding acidic or basic salt.

One skilled in the art will recognize that depending on the pH conditions of any isolation and/or purification work-up, the compound of formula (I-M2) is isolated in its neutral form, or as its corresponding basic (e.g. Li+ or Na+ or K+) or corresponding acidic (e.g. protonated) salt form.

The compound of formula (I-M7) may be prepared as described in more detail in Scheme 3, below.

Accordingly, n-butyl 4-(5-(4-cyano-1-((2-(trimethylsilyl) ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylate, prepared for example as described in Scheme 1 above, is reacted with a suitably selected reducing agent such as DIBAL, LiBH$_4$, and the like; in a suitably selected organic solvent such as THF, 1,4-dioxane, DME, and the like; at a temperature in the range of from about −80° C. to about 50° C., for example at about −30 to −40° C.; to yield 4-cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1-((2-(trimethylsilyl)ethoxy)methyl)-1H-imidazole-2-carboxamide.

The 4-cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1-((2-(trimethylsilyl)ethoxy)methyl)-1H-imidazole-2-carboxamide is reacted with a suitably selected desilylating reagent such as TBAF, KF, pyridinium hydrofluoride, and the like; in a suitably selected organic solvent such as THF, DME, 1,4-dioxane, and the like; at a temperature in the range of from about 0° C. to about 110° C., for example at about 60-65° C., heated by microwave; to yield 4-cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1-((2-(trimethylsilyl)ethoxy)methyl)-1H-imidazole-2-carboxamide, the compound of formula (I-M7).

In an embodiment, the present invention is directed to $D_4$-deuterated compounds of formula (I), more particularly, $D_4$-deuterated compounds of formula (I-M2) and $D_4$-deuterated compounds of formula (I-M7).

In another embodiment, the present invention is directed to a mixture of two $D_4$-deuterated regioisomers (or isotopomers) of the compound of formula (I-M2), more particularly, a mixture of a compound of formula (I-M2-D4a) and (I-M2-D4b)

(I-M2-D4a)

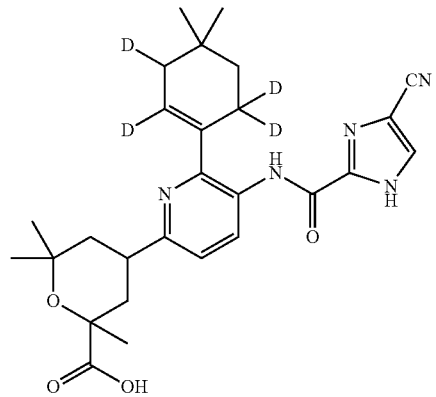

and (I-M2-D4b)

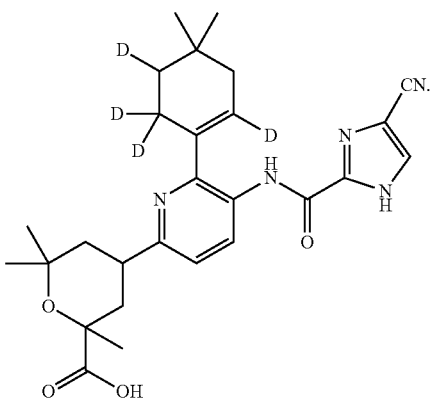

In another embodiment, the compound of formula (I-M2-D4a) and the compound of formula (I-M2-D4b) are present in a mixture at a molar ratio of about 1:1.

In another embodiment, the present invention is directed to a mixture of two $D_4$-deuterated regioisomers (or isotopomers) of the compound of formula (I-M7), more particularly, a mixture of a compound of formula (I-M7-D4a) and (I-M7-D4b)

(I-M7-D4a)

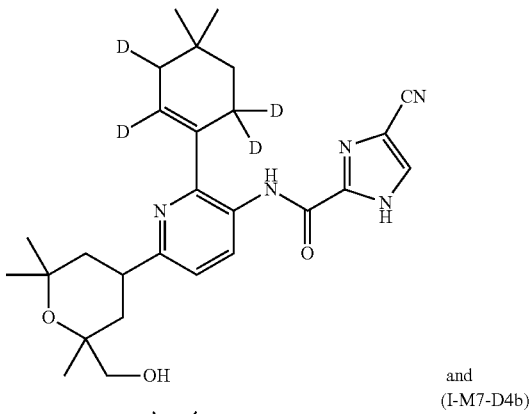

and
(I-M7-D4b)

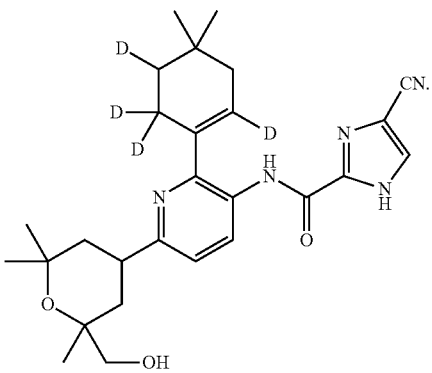

In another embodiment, the compound of formula (I-M7-D4a) and the compound of formula (I-M7-D4b) are present in a mixture at a molar ratio of about 1:1.

The $D_4$-deuterated compounds of formula (I-M2-D4a), (I-M2-D4b), (I-M7-D4a) and (I-M7-D4b) may be prepared as described in Schemes 1-3 above, substituting a mixture of 2',3',6',6'-[$D_4$]-deuterated and 2',5',6',6'-[$D_4$]-deuterated 2-(4,4-dimethylcyclohex-1-en-1-yl)-4,4,5,5-tetramethyl-1,3,2-dioxaborolanes for the corresponding (un-deuterated) 2-(4,4-dimethylcyclohex-1-en-1-yl)-4,4,5,5-tetramethyl-1,3,2-dioxaborolane compound, and reacting as therein described.

The mixture of (isotopomers) 2',3',6',6'-[$D_4$]-deuterated and 2',3',6',6'-[$D_4$]-deuterated 2-(4,4-dimethylcyclohex-1-en-1-yl)-4,4,5,5-tetramethyl-1,3,2-dioxaborolanes may be prepared, for example, as described in Scheme 4, below.

Scheme 4

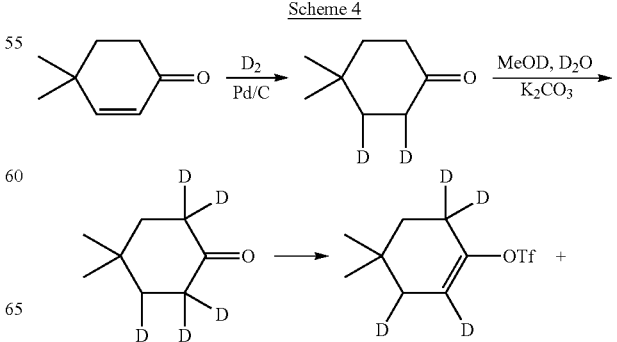

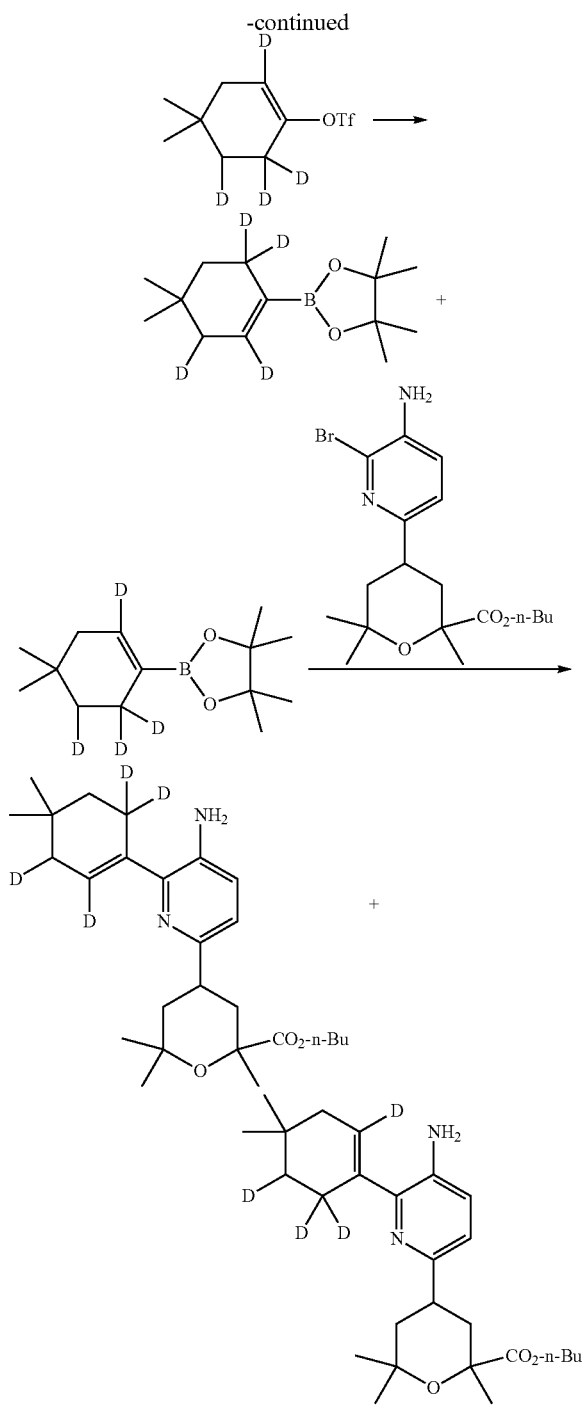

Accordingly, 4,4-dimethylcyclohex-2-enone, a known compound or compound prepared by known methods, is deuterated by reacting with $D_2$ (gas) in the presence of a suitably selected catalyst such as Pd/C, and the like; in a suitably selected solvent such as deuterated methanol, and the like; to yield the corresponding (2S,3R)-2,3-di-deuterated-4,4-dimethylcyclohexanone.

The 2,3-di-deuterated-4,4-dimethylcyclohexanone is further reacted with $CD_3OD$ (deuterated methanol) in the presence of a suitably selected inorganic base such as $K_2CO_3$; in $D_2O$ (deuterated water); to yield the corresponding 2,2',3',6',6'-penta-deuterated-4,4-dimethylcyclohexanone.

The 2,2',3',6',6'-penta-deuterated-4,4-dimethylcyclohexanone is triflated by reacting with a suitably selected source of triflate such as $PhN(Tf)_2$, and the like; upon the treatment of a suitably selected base such as LDA, and the like; in a suitably selected solvent such as THF, and the like; to yield a mixture of the corresponding 2',3',6',6'-tetra-deuterated-4,4-dimethylcyclohex-1-en-1-yl trifluoromethanesulfonate and 2',5',6',6'-tetra-deuterated-4,4-dimethylcyclohex-1-en-1-yl trifluoromethanesulfonate.

The mixture of 2',3',6',6'-tetra-deuterated-4,4-dimethylcyclohex-1-en-1-yl trifluoromethanesulfonate and 2',5',6',6'-tetra-deuterated-4,4-dimethylcyclohex-1-en-1-yl trifluoromethanesulfonate is reacted with bis(pinacolate)diboron, a known compound; in the presence of a suitably selected catalyst such as Pd, and the like; in a suitably selected solvent such as 1,4-dioxane, and the like; to yield the a mixture of the corresponding 2',3',6',6'-tetra-deuterated-2-(-4,4-dimethylcyclohex-1-en-1-yl)-4,4,5,5-tetramethyl-1,3,2-dioxaborolane and the corresponding 2',5',6',6'-tetra-deuterated-2-(4,4-dimethylcyclohex-1-en-1-yl)-4,4,5,5-tetramethyl-1,3,2-dioxaborolane.

The mixture of 2',3',6',6'-tetra-deuterated-2-(-4,4-dimethylcyclohex-1-en-1-yl)-4,4,5,5-tetramethyl-1,3,2-dioxaborolane and 2',5',6',6'-tetra-deuterated-2-(4,4-dimethylcyclohex-1-en-1-yl)-4,4,5,5-tetramethyl-1,3,2-dioxaborolane is reacted with n-butyl 4-(5-amino-6-bromopyridin-2-yl)-2,6,6-trimethyltetrahydro-2H-pyran-2-carboxylate, a known compound or compound prepared by known methods; in the presence of a suitably selected coupling agent such as $Pd(PPh_3)_2Cl_2$, $Pd(dppf)_2Cl_2$, $Pd(dba)_2Cl_2$, and the like; in the presence of a suitably selected inorganic base such as $Na_2CO_3$, KOAc, $Cs_2CO_3$, and the like; in a suitably selected solvent or mixture of solvents such as a mixture of 1,4-dioxane and water, DME, 1,4-dioxane, and the like; to yield a mixture of the corresponding 2',3',6',6'-tetra-deuterated-n-butyl 4-(5-amino-6-(4,4-dimethylcyclohex-1-en-1-yl)pyridin-2-yl)-2,6,6-trimethyltetrahydro-2H-pyran-2-carboxylate and the corresponding 2',5',6',6'-tetra-deuterated-n-butyl 4-(5-amino-6-(4,4-dimethylcyclohex-1-en-1-yl)pyridin-2-yl)-2,6,6-trimethyltetrahydro-2H-pyran-2-carboxylate.

One skilled in the art will recognize that the mixture of 2',3',6',6'-$[D_4]$-deuterated and 2',5',6',6'-$[D_4]$-deuterated 2-(4,4-dimethylcyclohex-1-en-1-yl)-4,4,5,5-tetramethyl-1,3,2-dioxaborolanes is then substituted for the corresponding (un-deuterated) 2-(4,4-dimethylcyclohex-1-en-1-yl)-4,4,5,5-tetramethyl-1,3,2-dioxaborolane in Scheme 1, and reacted with potassium 4-cyano-1-((2-(trimethylsilyl)ethoxy)methyl)-1H-imidazole-2-carboxylate, as therein described, to yield a mixture of 2',3',6',6'-$[D_4]$-deuterated and 2',5',6',6'-$[D_4]$-deuterated n-butyl 4-(5-(4-cyano-1-((2-(trimethylsilyl)ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylate.

The mixture of 2',3',6',6'-$[D_4]$-deuterated and 2',5',6',6'-$[D_4]$-deuterated n-butyl 4-(5-(4-cyano-1-((2-(trimethylsilyl)ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylates is substituted for the corresponding (un-deuterated) n-butyl 4-(5-(4-cyano-1-((2-(trimethylsilyl)ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylate in Scheme 2 above, and reacted as therein described, to yield a mixture of the compound of formula (I-M2-D4a) and compound of formula (I-M2-D4b).

Alternatively, the mixture of 2',3',6',6'-$[D_4]$-deuterated and 2',5',6',6'-$[D_4]$-deuterated n-butyl 4-(5-(4-cyano-1-((2-

(trimethylsilyl)ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylates is substituted for the corresponding (un-deuterated) n-butyl 4-(5-(4-cyano-1-((2-(trimethylsilyl)ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylate in Scheme 3 above, and reacted as therein described, to yield a mixture of the compound of formula (I-M7-D4a) and compound of formula (I-M7-D4b).

In an embodiment, the present invention is directed to a mixture of the 2',3',6',6'-[D4]-deuterated and the 2',5',6',6'-[D4]-deuterated compound of formula (P), herein referred to as the compound of formula (P-D4a) and the compound of formula (P-D4b), respectively.

The compound of formula (P-D4a) and the compound of formula (P-D4b) may be prepared according to the process as described in Scheme 5, below.

Scheme 5

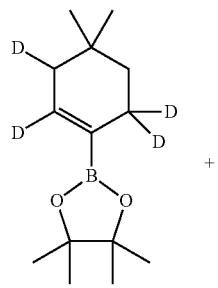

+

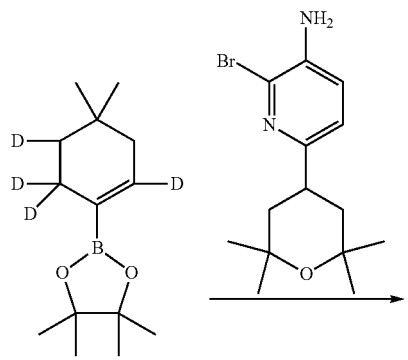

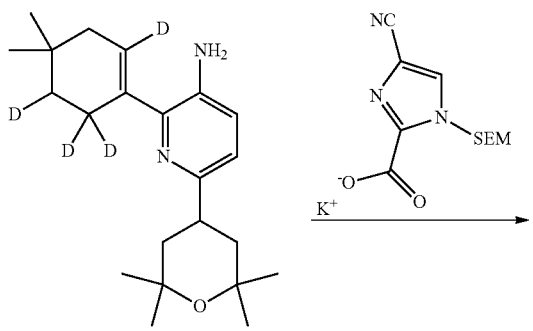

-continued

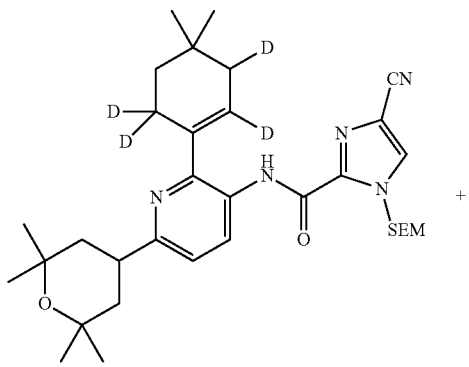

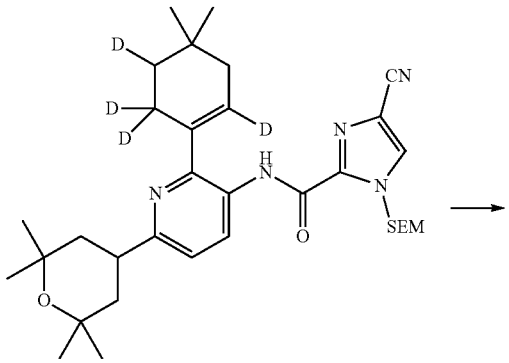

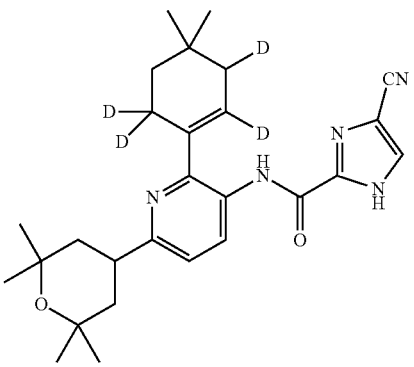

+

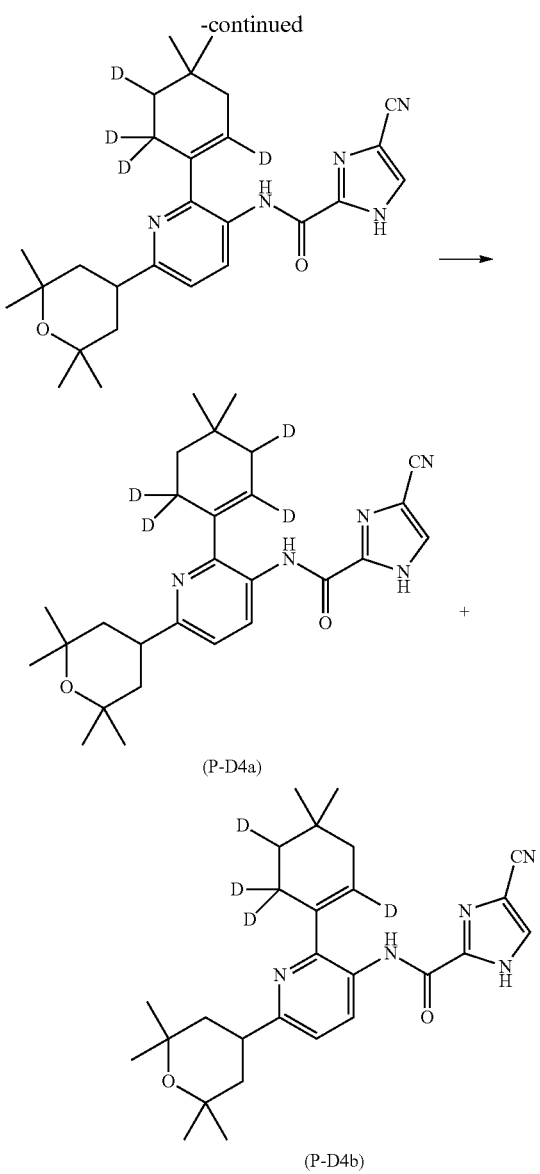

(P-D4a)

(P-D4b)

Accordingly, a mixture of 2',3',6',6'-[$D_4$]-deuterated 2-(4,4-dimethylcyclohex-1-en-1-yl)-4,4,5,5-tetramethyl-1,3,2-dioxaborolane and 2',5',6',6'-[$D_4$]-deuterated 2-(4,4-dimethylcyclohex-1-en-1-yl)-4,4,5,5-tetramethyl-1,3,2-dioxaborolane is reacted with 2-bromo-6-(2,2,6,6-tetramethyltetrahydro-2H-pyran-4-yl)pyridin-3-amine, a known compound or compound prepared by known methods, in the presence of a suitably selected coupling agent such as Pd(PPh$_3$)$_2$Cl$_2$, Pd(dppf)$_2$Cl$_2$, Pd(dba)$_2$Cl$_2$, and the like; in the presence of a suitably selected inorganic base such as Na$_2$CO$_3$, KOAc, Cs$_2$CO$_3$, and the like; in a suitably selected solvent or mixture of solvents such as a mixture of 1,4-dioxane and water, DME, 1,4-dioxane, and the like; to yield a mixture of the corresponding 2',3',6',6'-[$D_4$]-deuterated and 2',5',6',6'-[$D_4$]-deuterated 2-(4,4-dimethylcyclohex-1-en-1-yl)-6-(2,2,6,6-tetramethyltetrahydro-2H-pyran-4-yl)pyridin-3-amines.

The mixture of 2, 2',3',6',6'-[$D_4$]-deuterated and 2',5',6',6'-[$D_4$]-deuterated 2-(4,4-dimethylcyclohex-1-en-1-yl)-6-(2,2,6,6-tetramethyltetrahydro-2H-pyran-4-yl)pyridin-3-ami is reacted with potassium 4-cyano-1-((2-(trimethylsilyl)ethoxy)methyl)-1H-imidazole-2-carboxylate, a known compound; in the presence of a suitably selected coupling reagent such as PyBrop, DCC, EDCI, and the like; in the presence of a suitably selected organic base such as DIPEA, TEA, pyridine, and the like; in a suitably selected organic solvent such as DCM, DCE, THF, and the like; to yield a mixture of the corresponding 2',3',6',6'-[$D_4$]-deuterated and 2',5',6',6'-[$D_4$]-deuterated 4-cyano-N-(2-(4,4-dimethylcyclohex-1-en-1-yl)-6-(2,2,6,6-tetramethyltetrahydro-2H-pyran-4-yl)pyridin-3-yl)-1-((2-(trimethylsilyl)ethoxy)methyl)-1H-imidazole-2-carboxamides.

The mixture of 2',3',6',6'-[$D_4$]-deuterated and 2',5',6',6'-[$D_4$]-deuterated 4-cyano-N-(2-(4,4-dimethylcyclohex-1-en-1-yl)-6-(2,2,6,6-tetramethyltetrahydro-2H-pyran-4-yl)pyridin-3-yl)-1-((2-(trimethylsilyl)ethoxy)methyl)-1H-imidazole-2-carboxamides is reacted to remove the SEM protecting group, reacting with a suitably selected desilylating reagent such as TBAF, KF, pyridinium hydrofluoride, and the like; in a suitably selected organic solvent such as THF, 1,4-dioxane, diethyl ether, and the like; at a temperature in the range of from about 0° C. to about 120° C., for example at about 60-65° C., heated by microwave; to yield a mixture of 2',3',6',6'-[$D_4$]-deuterated and 2',5',6',6'-[$D_4$]-deuterated 4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamides.

The mixture of 2',3',6',6'-[$D_4$]-deuterated and 2',5',6',6'-[$D_4$]-deuterated 4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamides is reacted with a suitably selected acid or base such as LiOH, NaOH, KOH, and the like; in a suitably selected solvent such as water, MeOH, EtOH, and the like; to yield a mixture of the corresponding 2',3',6',6'-[$D_4$]-deuterated and 2',5',6',6'-[$D_4$]-deuterated 4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamides.

Pharmaceutical Compositions

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention further comprises pharmaceutical compositions containing one or more compounds of formula (I), prepared as described herein, with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.05 mg/kg/day to about 15.0 mg/kg/day, or any amount or range therein, preferably from about 0.1 mg/kg/day to about 10.0 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating c-FMS kinase mediated disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by c-FMS kinase is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 500 mg/kg of body weight per day, or any amount or range therein. Preferably, the range is from about 0.1 to about 50.0 mg/kg of body weight per day, or any amount or range therein. More preferably, from about 0.5 to about 15.0 mg/kg of body weight per day, or any amount or range therein. More preferably, from about 1.0 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

SYNTHESIS EXAMPLES

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1: (Compound of Formula (I-M7))

Preparation of 4-cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1H-imidazole-2-carboxamide

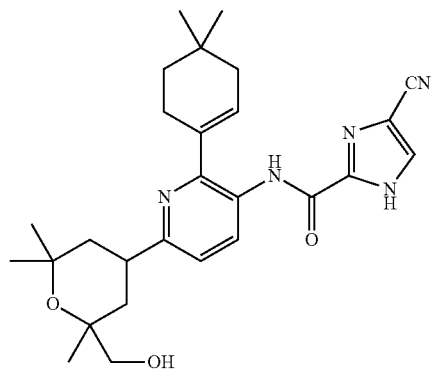 [SMILES: CC1(C)CC=C(c2nc(C3CC(C)(C)OC(C)(CO)C3)ccc2NC(=O)c2nc(C#N)c[nH]2)CC1]

Step A: n-butyl 9,9-dimethyl-1,4,8-trioxaspiro[4.5]dec-6-ene-7-carboxylate

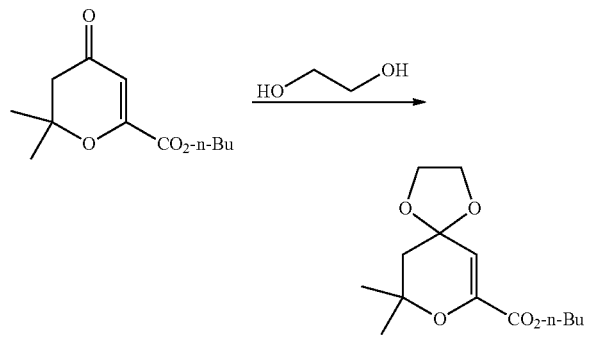

A mixture of n-butyl 2,2-dimethyl-4-oxo-3,4-dihydro-2H-pyran-6-carboxylate (25 g, 111 mmol), ethylene glycol (31 mL), and PPTS (0.825 g, 3.17 mmol) in toluene (400 mL) was stirred at 150° C. for 3 days. The resulting mixture was concentrated in vacuo to yield a residue (35 g) which was purified by column (petroleum ether/ethyl acetate=200/1 to 50:1) to yield n-butyl 9,9-dimethyl-1,4,8-trioxaspiro[4.5]dec-6-ene-7-carboxylate (20 g, 67%).

$^1$H NMR: (CDCl$_3$, 400 MHz): δ 5.82 (s, 1H), 4.12 (t, J=6.8 Hz, 2H), 3.96-3.90 (m, 4H), 1.95 (s, 2H), 1.62~1.56 (m, 2H), 1.34-1.29 (m, 8H), 0.87 (t, J=6.8 Hz, 3H).

Step B: n-butyl 9,9-dimethyl-1,4,8-trioxaspiro[4.5]decane-7-carboxylate

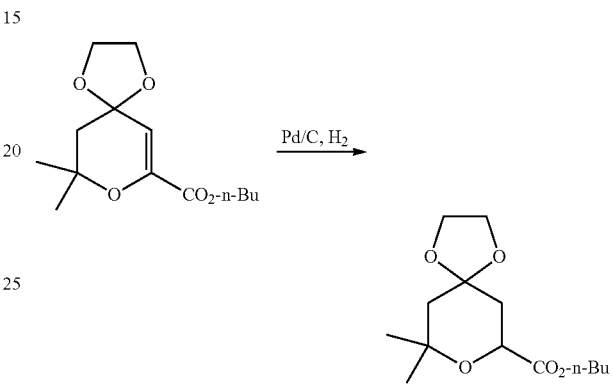

A mixture of n-butyl 9,9-dimethyl-1,4,8-trioxaspiro[4.5] dec-6-ene-7-carboxylate (38 g, 141 mmol) and Pd/C (10 g) in ethyl acetate (300 mL) was stirred at 40° C. at a pressure of 40 Psi with hydrogen overnight. The resulting mixture was filtered, and the filtrate was concentrated under vacuo to yield n-butyl 9,9-dimethyl-1,4,8-trioxaspiro[4.5]decane-7-carboxylate (38 g, 99%) as white solid.

$^1$H NMR: (CDCl$_3$, 400 MHz): δ4.35 (dd, J=12 Hz, 2.0 Hz, 1H), 4.14~4.10 (m, 2H), 4.06~3.91 (m, 2H), 3.90~3.87 (m, 2H), 1.95~1.92 (m, 1H), 1.70~1.60 (m, 5H), 1.34~1.29 (m, 8H), 0.87 (t, J=6.8 Hz, 3H).

Step C: n-butyl 7,9,9-trimethyl-1,4,8-trioxaspiro[4,5]decane-7-carboxylate

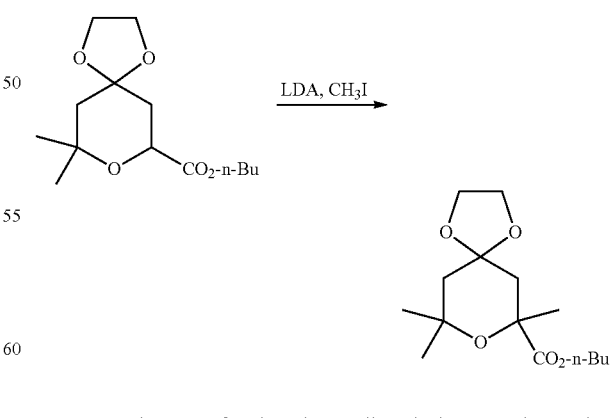

To a mixture of n-butyl 9,9-dimethyl-1,4,8-trioxaspiro[4.5]decane-7-carboxylate (28 g, 100 mmol) in THF was added dropwise LDA (2M, 110 mmol) at −78° C. and the resulting mixture stirred at −78° C. for 2 hrs. CH$_3$I (25.8 g, 150 mmol) was then added dropwise to the mixture at −78°

C. After the reaction completed, the resulting mixture was allowed to warm to room temperature and stirred overnight. The resulting mixture was quenched by water, concentrated under vacuo to yield a residue of n-butyl 7,9,9-trimethyl-1,4,8-trioxaspiro[4.5]decane-7-carboxylate (29 g, 99%), which was used in the next step without further purification.

$^1$H NMR: (CDCl$_3$, 400 MHz): δ4.19-4.02 (m, 2H), 4.00~3.90 (m, 4H), 2.65 (d, J=14 Hz, 2H), 1.70~1.56 (m, 2H), 1.53~1.49 (m, 1H), 1.48~1.37 (m, 5H), 1.32 (s, 3H), 0.87 (t, J=6.8 Hz, 3H).

Step D: n-butyl 2,6,6-trimethyl-4-oxotetrahydro-2H-pyran-2-carboxylate

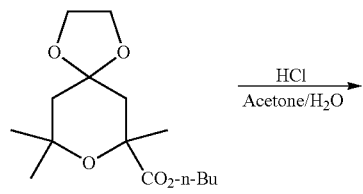

A mixture of n-butyl 7,9,9-trimethyl-1,4,8-trioxaspiro[4.5]decane-7-carboxylate (8 g, 28.0 mmol) in acetone (40 mL) and HCl aqueous solution (2M, 2 mL) was stirred at room temperature overnight. The resulting mixture was concentrated in vacuo and the residue was purified by flash chromatography on silica gel to yield n-butyl 2,6,6-trimethyl-4-oxotetrahydro-2H-pyran-2-carboxylate (6.8 g, 73.5%).

$^1$H NMR: (CDCl$_3$, 400 MHz): δ4.20-4.08 (m, 2H), 3.13-3.08 (d, J=16.8 Hz, 1H), 2.51-2.32 (m, 2H), 1.71-1.61 (m, 2H), 1.53 (s, 3H), 1.44-1.35 (m, 2H), 1.32-1.28 (m, 6H), 0.87 (t, J=6.8 Hz, 3H).

Step E: Mixture of n-butyl 2,6,6-trimethyl-4-(((trifluoromethyl)sulfonyl)oxy)-5,6-dihydro-2H-pyran-2-carboxylate and n-butyl 2,6,6-trimethyl-4-(((trifluoromethyl)sulfonyl)oxy)-3,6-dihydro-2H-pyran-2-carboxylate

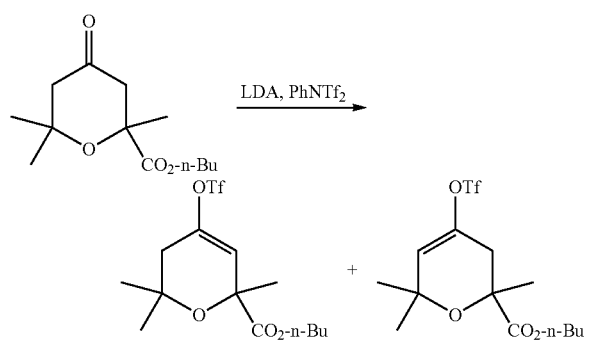

To a mixture of n-butyl 2,6,6-trimethyl-4-oxotetrahydro-2H-pyran-2-carboxylate (21 g, 86.4 mmol) in THF (500 mL) was added dropwise LDA (1.1M, 112 mmol) at −78° C. and the resulting mixture stirred at −78° C. for 2 hrs. PhNTf$_2$ (42 g, 117.6 mmol) was then added dropwise to the mixture at −78° C. After addition, the resulting mixture was allowed to warm to room temperature and stirred overnight. The reaction was then quenched with water, and the resulting mixture concentrated in vacuo to yield mixture of n-butyl 2,6,6-trimethyl-4-(((trifluoromethyl)sulfonyl)oxy)-5,6-dihydro-2H-pyran-2-carboxylate and n-butyl 2,6,6-trimethyl-4-(((trifluoromethyl)sulfonyl)oxy)-3,6-dihydro-2H-pyran-2-carboxylate (22 g, crude), which was used in the next step without further purification.

Step F: Mixture of n-butyl 2,6,6-trimethyl-4-(4,4,5,5-tetramethyl-1,3,2-dioxaborolan-2-yl)-5,6-dihydro-2H-pyran-2-carboxylate and n-butyl 2,6,6-trimethyl-4-(4,4,5,5-tetramethyl-1,3,2-dioxaborolan-2-yl)-3,6-dihydro-2H-pyran-2-carboxylate

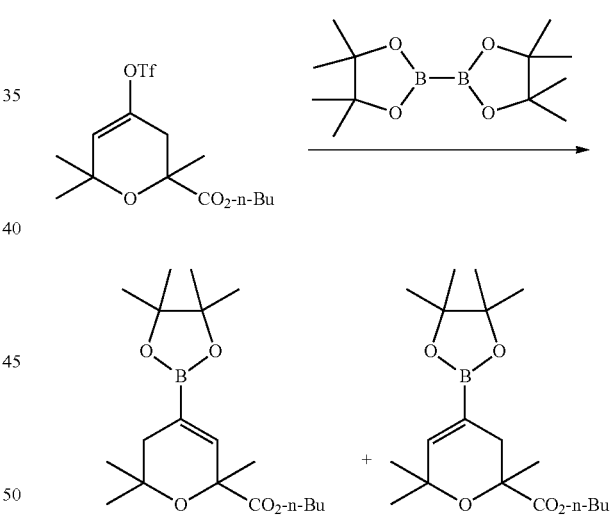

A mixture of n-butyl 2,6,6-trimethyl-4-(((trifluoromethyl)sulfonyl)oxy)-5,6-dihydro-2H-pyran-2-carboxylate and n-butyl 2,6,6-trimethyl-4-(((trifluoromethyl)sulfonyl)oxy)-3,6-dihydro-2H-pyran-2-carboxylate (22 g, 58.82 mmol), Pd(dppf)$_2$Cl$_2$ (5.88 g, 5.88 mmol), KOAc (17.2 g, 176.46 mmol), dppf (3.2 g, 5.88 mmol), bis(pinacolato)diboron (17.9 g, 70.58 mmol) in 1,4-dioxane was stirred at 100° C. overnight. The resulting mixture was concentrated in vacuo and the residue purified by flash chromatography on silica gel to yield a mixture of n-butyl 2,6,6-trimethyl-4-(4,4,5,5-tetramethyl-1,3,2-dioxaborolan-2-yl)-5,6-dihydro-2H-pyran-2-carboxylate and n-butyl 2,6,6-trimethyl-4-(4,4,5,5-tetramethyl-1,3,2-dioxaborolan-2-yl)-3,6-dihydro-2H-pyran-2-carboxylate (25 g, crude), which was used for next step without further purification.

Step G: Mixture of n-Butyl 2,6,6-trimethyl-4-(5-nitropyridin-2-yl)-5,6-dihydro-2H-pyran-2-carboxylate and n-Butyl 2,6,6-trimethyl-4-(5-nitropyridin-2-yl)-3,6-dihydro-2H-pyran-2-carboxylate

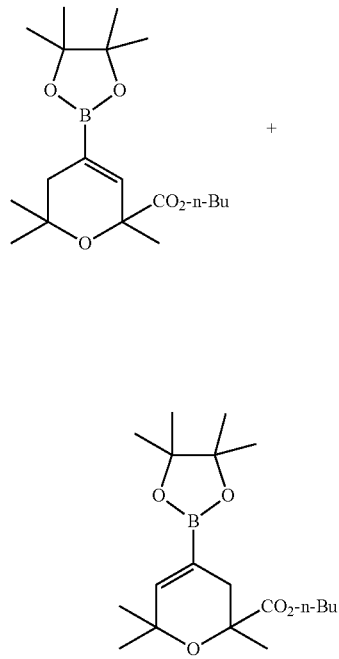

Step H: n-Butyl 4-(5-aminopyridin-2-yl)-2,6,6-trimethyltetrahydro-2H-pyran-2-carboxylate

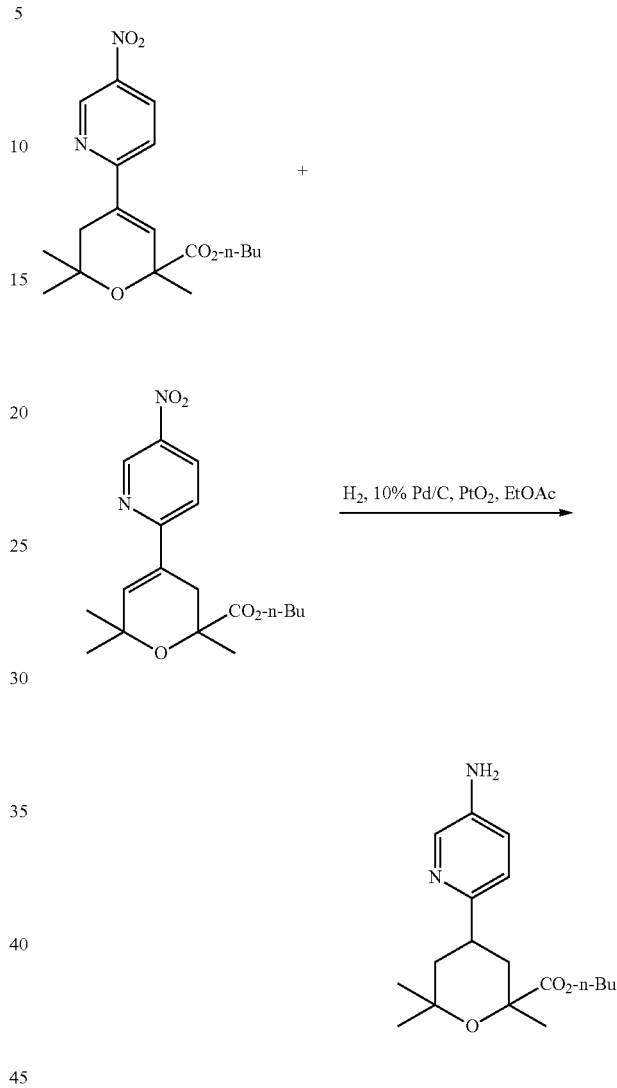

A mixture of n-butyl 2,6,6-trimethyl-4-(4,4,5,5-tetramethyl-1,3,2-dioxaborolan-2-yl)-5,6-dihydro-2H-pyran-2-carboxylate and n-butyl 2,6,6-trimethyl-4-(4,4,5,5-tetramethyl-1,3,2-dioxaborolan-2-yl)-3,6-dihydro-2H-pyran-2-carboxylate (1.3 g, 3.7 mmol), 2-bromo-5-nitro-pyridine (747 mg, 3.7 mmol), Pd(dppf)$_2$Cl$_2$ (0.26 g, 0.37 mmol), Na$_2$CO$_3$ (0.59 g, 0.57 mmol), dissolved in DME/EtOH/H$_2$O (2:1:1) (2 mL) was stirred at 120° C. in a microwave oven for 50 minutes. The resulting mixture was concentrated in vacuo and the residue was purified by chromatography on silica gel to yield a mixture of n-butyl 2,6,6-trimethyl-4-(5-nitropyridin-2-yl)-5,6-dihydro-2H-pyran-2-carboxylate and n-butyl 2,6,6-trimethyl-4-(5-nitropyridin-2-yl)-3,6-dihydro-2H-pyran-2-carboxylate (0.4 g).

$^1$H NMR: (CDCl$_3$, 400 MHz): δ 9.42 (s, 1H), 8.42 (d, J=6.0 Hz 1H), 7.68 (d, J=8.8 Hz, 1H), 7.13 (s, 1H), 4.22~4.21 (m, 2H), 2.67~2.63 (m, 1H), 2.53~2.43 (m, 1H), 1.71~1.67 (m, 2H), 1.62 (s, 3H), 1.59 (s, 3H), 1.47~1.35 (m, 2H), 1.21 (s, 3H), 0.87 (t, J=6.8 Hz, 3H). MS (M+1): 349.2

To a 500-ML hydrogenation bottle was added 1.89 grams of 10% palladium on charcoal and 0.12 grams of PtO$_2$, under N$_2$, and a solution of n-butyl 2,6,6-trimethyl-4-(5-nitropyridin-2-yl)-5,6-dihydro-2H-pyran-2-carboxylate and n-butyl 2,6,6-trimethyl-4-(5-nitropyridin-2-yl)-3,6-dihydro-2H-pyran-2-carboxylate (5.2 g) in ethyl acetate (40 mL). To the resulting suspension was connected into Parr shaker hydrogenation device and was applied with hydrogen at a pressure of 40 psi. After the reaction mixture was shaken under the hydrogen at a pressure of 40 psi for 4 days, analytic HPLC analysis indicated the starting material was consumed and reaction was completed. The resulting mixture water was filtrated through CELITE, and rinsed with ethyl acetate. The resulting solution was evaporated in vacuo to yield n-butyl 4-(5-aminopyridin-2-yl)-2,6,6-trimethyltetrahydro-2H-pyran-2-carboxylate as a yellow oil (5.2 g). ESI-MS (M+1) 321.

41

Step I: n-Butyl 4-(5-amino-6-bromopyridin-2-yl)-2,6,6-trimethyltetrahydro-2H-pyran-2-carboxylate

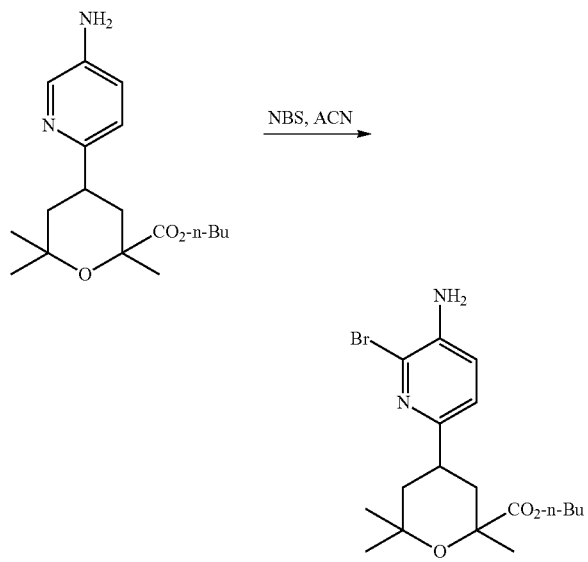

To a light brown solution of n-butyl 4-(5-aminopyridin-2-yl)-2,6,6-trimethyltetrahydro-2H-pyran-2-carboxylate (220 mg, 687 μmol, 1 equiv in acetonitrile (5 mL) in an ice-water bath was added N-bromosuccinimide (122 mg, 687 μmol, 1 equiv) in one portion. When TLC, HPLC and LCMS analysis indicated consumption of the starting material, a 10% aqueous solution of sodium thiosulfate (5 mL) was added and the resulting mixture stirred for 10 minutes. The solvent was removed in vacuo to yield a residue which was partitioned between ethyl acetate and saturated aqueous sodium bicarbonate. The organic phase was separated, dried over anhydrous magnesium sulfate; gravity filtered, and concentrated in vacuo to yield a red orange oil. The oil was purified over 12 grams of normal phase silica gel eluted with heptanes and ethyl acetate at 5 mL per minute in 8 mL fractions. The product rich fractions were pooled and concentrated in vacuo to yield n-butyl 4-(5-amino-6-bromopyridin-2-yl)-2,6,6-trimethyltetrahydro-2H-pyran-2-carboxylate (274 mg, >99% yield) as an orange oil. ESI-MS (M+1) 400.

Step J: n-Butyl 4-(5-amino-6-(4,4-dimethylcyclohex-1-en-1-yl)pyridin-2-yl)-2,6,6-trimethyltetrahydro-2H-pyran-2-carboxylate

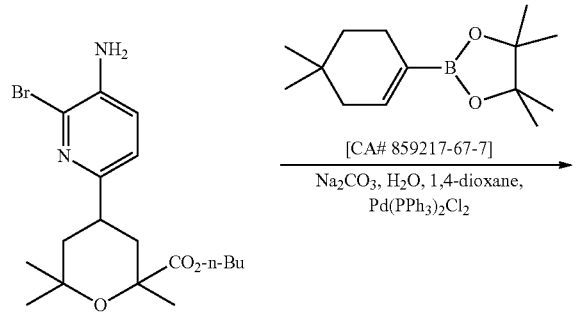

42

-continued

To a solution of n-butyl 4-(5-amino-6-bromopyridin-2-yl)-2,6,6-trimethyltetrahydro-2H-pyran-2-carboxylate (1.88 g, 4.71 mmol) in 1,4-dioxane (16 mL) was added 2-(4,4-dimethyl-cyclohex-1-enyl)-4,4,5,5-tetramethyl-[1,3,2]dioxaborolane (1.333 g, 5.65 mmol), Pd(PPh₃)₂Cl₂ (331 mg, 0.47 mmol), and 2M Na₂CO₃ (16 mL) at room temperature. The resulting mixture was stirred at 80° C. overnight. After the reaction was completed by TLC monitoring, water and ethyl acetate were added to yield a partition of two layers. The organic layer was separated and the aqueous layer was extracted with more ethyl acetate; the organic phases were combined, dried over Na₂SO₄, and concentrated in vacuo. The resulting residue was purified by chromatography on a silica gel column with a gradient 0-100% ethyl acetate/heptanes to yield n-butyl 4-(5-amino-6-(4,4-dimethylcyclohex-1-en-1-yl)pyridin-2-yl)-2,6,6-trimethyltetrahydro-2H-pyran-2-carboxylate as a brown oil. ESI-MS (M+1) 429.

Step K: n-Butyl 4-(5-(4-cyano-1-((2-(trimethylsilyl)ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylate

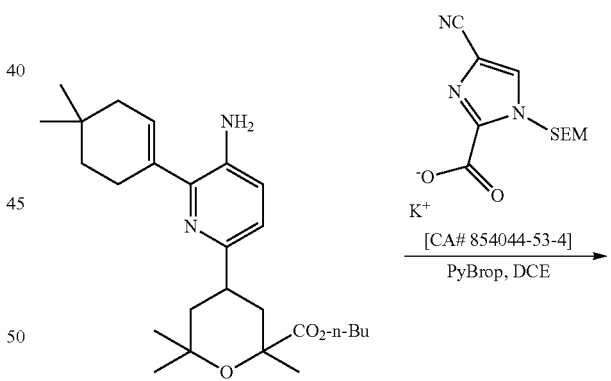

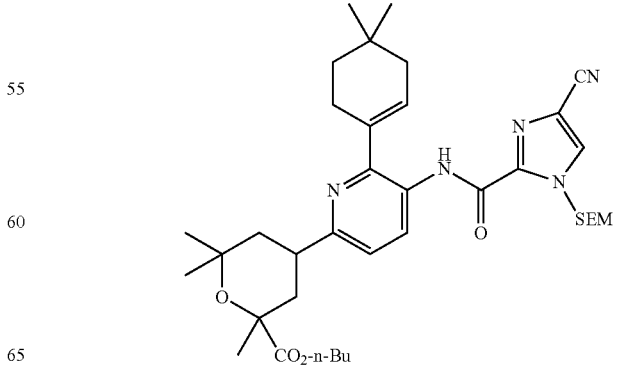

To a solution of n-butyl 4-(5-amino-6-(4,4-dimethylcyclohex-1-en-1-yl)pyridin-2-yl)-2,6,6-trimethyltetrahydro-2H-pyran-2-carboxylate (0.761 g, 1.775 mmol) in dichloroethane (12 mL), potassium salt of 4-cyano-1-(2-trimethylsilanyl-ethoxymethyl)-1H-imidazole-2-carboxylic acid (0.75 g, 2.48 mmol), PyBrop (1.24 g, 2.66 mmol), diisopropylethylamine (619 uL, 3.55 mmol) were added. The resulting mixture was then stirred at room temperature overnight. The resulting mixture was then partitioned by addition of water and dichloromethane. Organic layer was separated and aqueous layer was extracted with more dichloromethane. The organic phases were combined, dried over $Na_2SO_4$, and concentrated in vacuo. The resulting residue was purified by chromatography on a silica gel column with a gradient 0-100% ethyl acetate/heptanes to yield n-butyl 4-(5-(4-cyano-1-((2-(trimethylsilyl)ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylate as a foam (1.058 g). ESI-MS (M+1) 678.

Step L: 4-Cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1-((2-(trimethylsilyl)ethoxy)methyl)-1H-imidazole-2-carboxamide

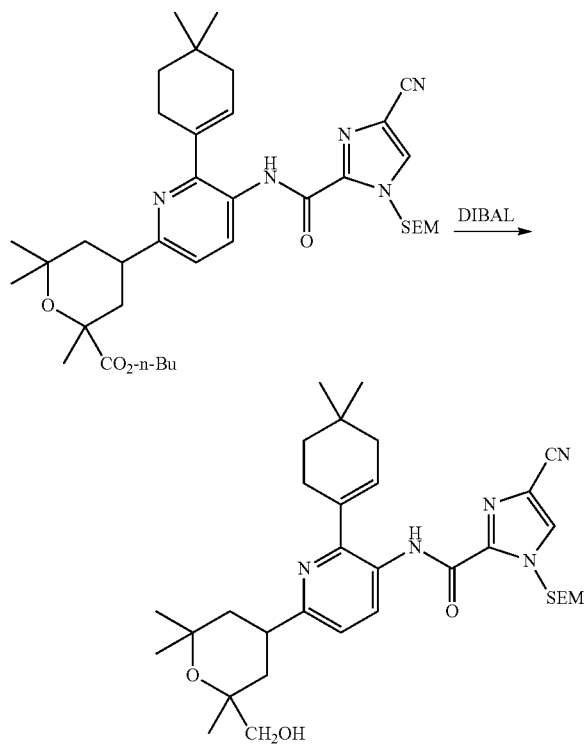

To a solution of n-butyl 4-(5-(4-cyano-1-((2-(trimethylsilyl)ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylate (0.415 g, 0.612 mmol) in THF (3 mL) at −30 to −40° C., was added in a 1M solution of DIBAL in THF (2.45 mL). The resulting mixture was then stirred at −5° C. overnight. To the resulting mixture, cooled at −40° C., was then added 1M solution of DIBAL in THF (1.3 mL). The resulting mixture was then stirred at −40° C. for three hours. The reaction was quenched by addition of ethyl acetate (9 mL) and saturated aqueous ammonium chloride (20 mL). The resulting mixture was then extracted with ethyl acetate. The organic phases were combined, dried over $Na_2SO_4$, filtrated through CELITE, and the solvent was removed in vacuo at 40° C. to yield 4-cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1-((2-(trimethylsilyl)ethoxy)methyl)-1H-imidazole-2-carboxamide as white foam (0.347 mg), which was used for next step without further purification. ESI-MS (M+1) 608.

Step M: 4-cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1H-imidazole-2-carboxamide (Compound of Formula (I-M7))

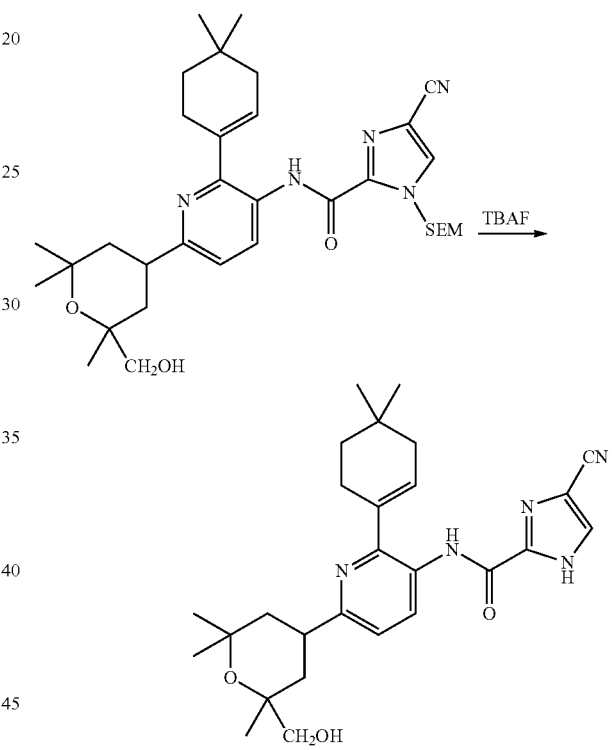

To a solution of -cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1-((2-(trimethylsilyl)ethoxy)methyl)-1H-imidazole-2-carboxamide (347 mg), was added a 1M THF solution of TBAF (3 mL). The resulting mixture was stirred at 60-65° C. overnight. After the reaction was cooled to room temperature, the residue was purified by chromatography on silica gel column with gradient 0-100% ethyl acetate/heptanes to yield 4-cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1H-imidazole-2-carboxamide.

$^1$H NMR: (CDCl$_3$, 400 MHz): δ (ppm) 12.0 (s, 1H), 9.75 (s, 1H), 8.60 (d, 1H), 7.70 (s, 1H), 7.20 (d, 1H), 6.0 (s, 1H), 3.50 (d, 1H), 3.40-3.30 (m, 2H), 2.60 (br, 1H), 2.50 (br, 2H), 2.15 (s, 2H), 2.02 (t, 1H), 1.90 (m, 1H), 1.30-1.50 (m, 4H), 1.40 (s, 3H), 1.35-1.25 (m, 6H), 1.12 (s, 6H). Calculated for $C_{27}H_{35}N_5O_3 \cdot 0.03H_2O$ is C, 67.82; H, 7.39; N, 14.65. Found C, 67.82; H, 7.12; N, 14.08. ESI-MS (M+1) 478.

Example 2: (Compound of Formula (I-M2))

Preparation of 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylic acid

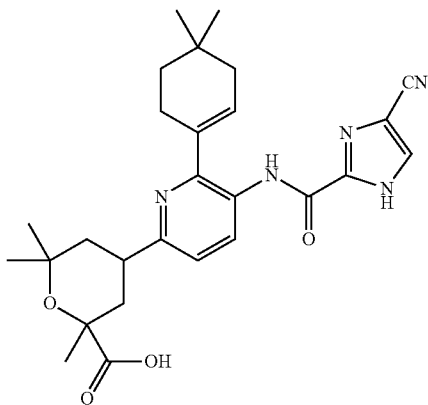 [SMILES: CC1(C)CC=C(c2nc(C3CC(C)(C)OC(C)(C(=O)O)C3)ccc2NC(=O)c2nc(C#N)c[nH]2)CC1]

Step A: n-Butyl 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylate

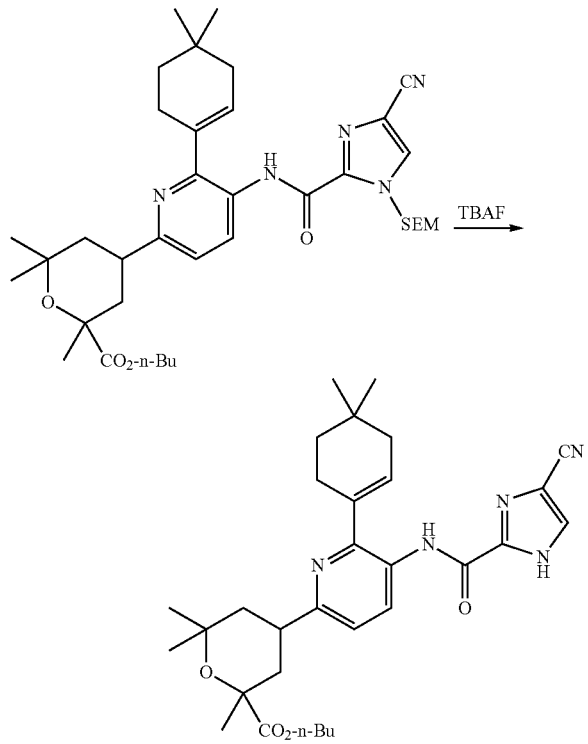

To a THF solution (2 mL) of n-butyl 4-(5-(4-cyano-1-((2-(trimethylsilyl)ethoxy)methyl)-1H-imidazole-2-carboxamido)-6-(4,4-dimethylcyclohex-1-en-1-yl)pyridin-2-yl)-2,6,6-trimethyltetrahydro-2H-pyran-2-carboxylate (386 mg, 0.57 mmol), prepared as described in Step K of Example 1 above, was added a 1M THF solution of TBAF (2.9 mL). The resulting mixture was stirred and heated at 62° C. in a microwave oven for 20 hours, at which time TLC and LCMS analysis indicated the starting material was consumed and reaction was completed. MS m/z 548 (MH$^+$). The resulting mixture, containing n-butyl 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylate was used in the next step without further purification.

Step B: 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylic acid

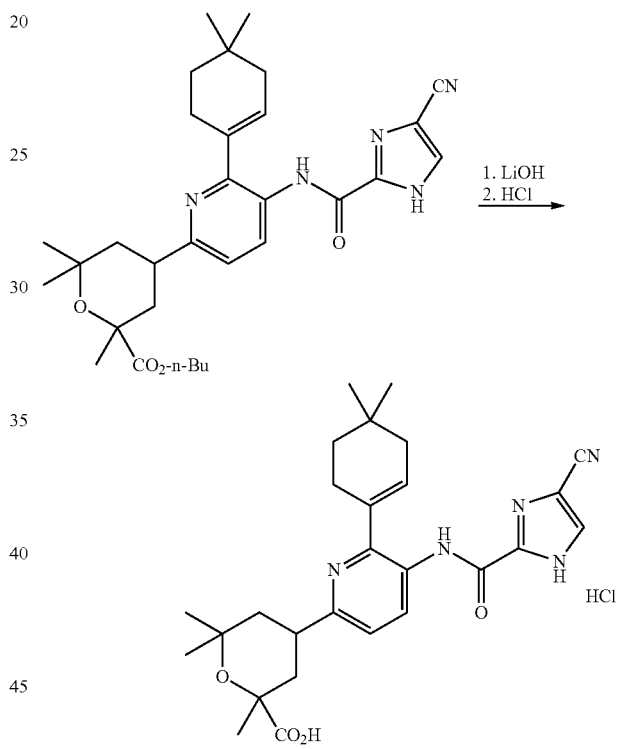

To a solution of n-butyl 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylate (0.114 mmol) in THF (1 mL) was added a solution of lithium hydroxide (6 mg) in water (1 mL). The resulting mixture was stirred at room temperature overnight and then acidified with aqueous hydrochloric acid to pH 5. The resulting solution was evaporated in vacuo and the residue subjected to chromatography separation on silica gel column with gradient 0-100% ethyl acetate/heptanes to yield 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylic acid as a white solid (37 mg, 66%).

$^1$H NMR: (CDCl$_3$, 400 MHz): δ (ppm) 12.3 (s, 1H), 9.80 (s, 1H), 8.65 (d, 1H), 7.78 (s, 1H), 7.12 (d, 1H), 6.0 (s, 1H), 3.35 (m, 1H), 2.50 (m, 2H), 2.38 (d, 1H), 2.08 (br, 2H), 2.05-1.85 (m, 3H), 1.67 (s, 3H), 1.61 (m, 2H), 1.44 (s, 3H), 1.40 (s, 3H), 1.25 (m, 1H), 1.11 (s, 6H). MS m/z 492 (MH$^+$).

Elemental Analysis: Calculated for $C_{27}H_{33}N_5O_4$: C, 65.97; H, 6.77; N, 13.02. Measured: C, 65.19; H, 6.58; N, 12.81.

Example 3: (Mixture of Compound of Formula (I-M7-D4a) and (I-M7-D4b))

Mixture of 2',3',6',6'-[$D_4$]-deuterated and 2',5',6',6'-[$D_4$]-deuterated 4-cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1H-imidazole-2-carboxamide

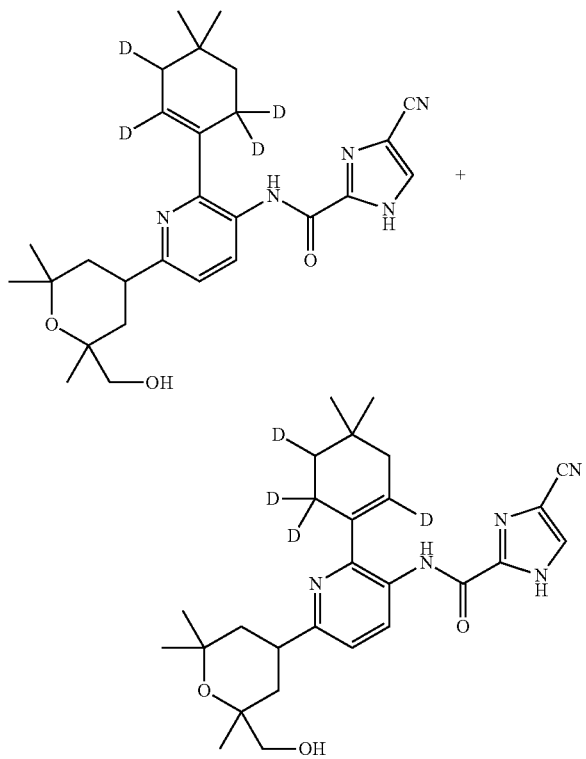

Step A: 2,3-[$D_2$]-deuterated 4,4-Dimethylcyclohexanone

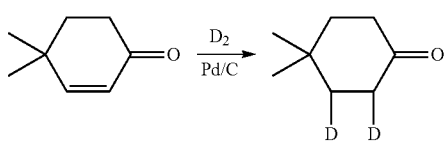

To a suspension of 4,4-dimethylcyclohexenone (20 g, 161 mmol) in diethyl ether was added 10% palladium on carbon (500 mg) under nitrogen atmosphere. The reaction vessel was evacuated and backfilled with deuterium gas. This process was repeated two additional times. The reaction mixture was stirred overnight under a balloon of deuterium gas. Conversion was monitored using $^1$H NMR (CDCl$_3$, 400 MHz) by periodically aliquotting a 250 µL sample, filtering through a syringe filter and concentrating in vacuo. Upon complete reduction (disappearance of the two olefin doublets δ 6.67 ppm and 5.83 ppm), nitrogen gas was bubbled through the resulting mixture to remove excess deuterium gas. The suspension was filtered through a bed of CELITE and the filtrate concentrated in vacuo (rotovap bath <30° C.) to yield 2,3-[$D_2$]-deuterated 4,4-dimethylcyclohexanone as a colorless oil (19.8 g, 96% yield). The oil was used in the next step without further purification. $^1$H NMR (CDCl$_3$, 400 MHz) δ 1.10 (s, 6H, CH$_3$), 1.62-1.70 (m, 3H, CH+CH$_2$), 2.30-2.37 (m, 3H, CH+CH2).

Step B: 2,2',5',6',6'[$D_5$]-deuterated 4,4-Dimethylcyclohexanone

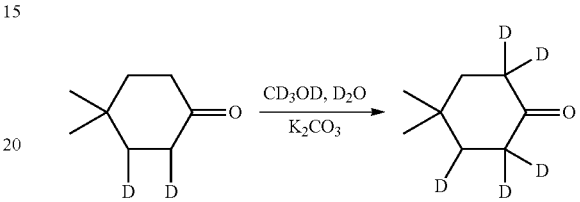

The 2,3-[$D_2$]-deuterated 4,4-dimethylcyclohexanone (19.8 g, 154 mmol) was partitioned between deuterated water (50 mL) and tetrahydrofuran (25 mL). To the biphasic mixture was added potassium carbonate (5.3 g, 38.6 mmol, 0.25 equiv) and the vessel heated in an 80° C. mantle overnight. The hydrogen-deuterium exchange incorporation was monitored using 1H NMR (CDCl3, 400 MHz) by monitoring the disappearance of the CHα protons at δ 2.45 ppm. Upon complete exchange, the phases were separated and the aqueous phase extracted with diethyl ether (three 25-mL portions). The combined organic phases were dried over sodium sulfate, gravity filtered and concentrated in vacuo to yield 2,2',5',6',6'-[$D_5$]-deuterated 4,4-dimethylcyclohexanone as a low melting colorless solid (19.0 g, 94% yield). Rf [normal phase silica gel, heptane-ethyl acetate 1:1] 0.67 (2,4-dinitrophenylhydrazine=orange); $^1$H NMR (CDCl3, 400 MHz) δ 1.10 (s, 6H, CH3), 1.64 (s, 1H, CH), 1.66 (s, 2H, CH2).

Step C: Mixture of 2',3',6',6'-[$D_4$]-deuterated and 2',5',6',6'-[$D_4$]-deuterated 4,4-dimethylcyclohex-1-en-1-yl trifluoromethanesulfonates

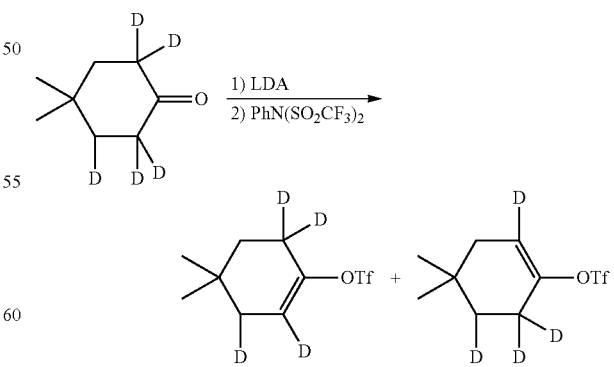

A 100 mL single neck round bottom flask with stirbar was charged with 2,2',5',6',6'-[$D_5$]-deuterated 4,4-dimethylcyclohexanone (3.00 g, 22.9 mmol, 1 equiv) and tetrahydrofuran (46 mL) to give a colorless solution. The reaction vessel was cooled in a dry ice-acetone bath for 30 minutes, prior to the addition of lithium diisopropylamide (2.0 M, 12.6 mL, 25.2 mmol, 1.1 equiv) in five 2.5-mL portions via Hamilton 2.5 mL gas tight syringe with 6 inch 18 gauge stainless steel needle. The resulting reddish-orange reaction mixture was aged in the dry ice-acetone bath for 30 minutes. A solution of 1,1,1-trifluoro-N-phenyl-N-((trifluoromethyl)sulfonyl)methanesulfonamide (6.45 g, 22.9 mmol, 1 equiv) in tetrahydrofuran (10 mL) was cannulated under positive nitrogen pressure. The reaction mixture was stirred for one hour then quenched by the addition of saturated aqueous ammonium chloride (25 mL). The biphasic mixture was stirred vigorously and allowed to warm to room temperature over a one hour period. The phases were separated and the aqueous phase extracted with ethyl acetate (two 25-mL portions). The combined organic phases were washed with water (20-mL), dried over anhydrous magnesium sulfate, and gravity filtered. The filtrate was concentrated in vacuo to yield an oil that contained pyridine impurities by 1H NMR (400 MHz). The oil was purified over a REDISEP 120 gram normal phase silica gel column eluted with heptane-ethyl acetate gradient in 25 mL fractions. The product rich fractions were pooled and concentrated in vacuo to yield a mixture of 2',3',6',6'-[$D_4$]-deuterated and 2',5',6',6'-[$D_4$]-deuterated 4,4-dimethylcyclohex-1-en-1-yl trifluoromethanesulfonates (3.65 g, 61% yield). $^{19}F$ NMR (CDCl3, 376 MHz) δ −74.1.

Step D: Mixture of 2',3',6',6'-[$D_4$]-deuterated and 2',5',6',6'-[$D_4$]-deuterated 2-(4,4-dimethylcyclohex-1-en-1-yl)-4,4,5,5-tetramethyl-1,3,2-dioxaborolanes

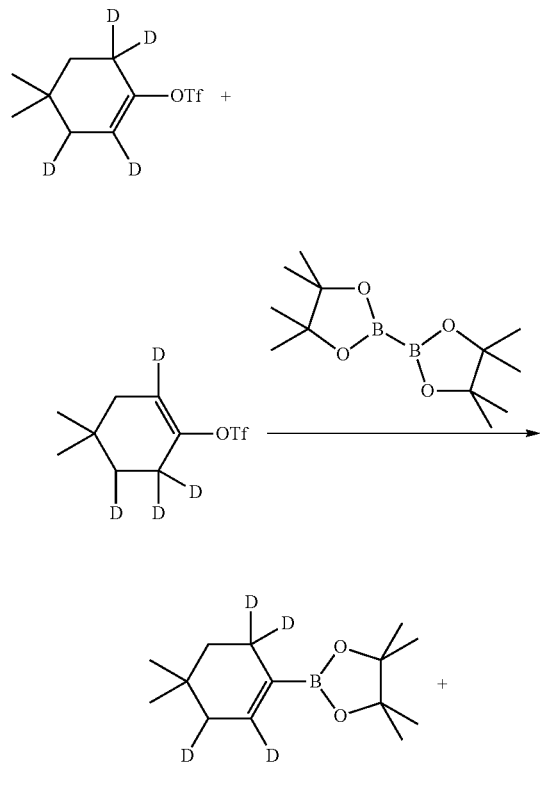

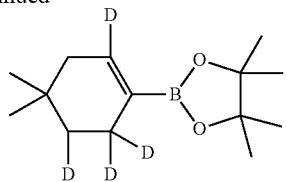

A 100 mL single neck round bottom flask with stirbar was charged with the mixture of 2',3',6',6'-[$D_4$]-deuterated and 2',5',6',6'-[$D_4$]-deuterated 4,4-dimethylcyclohex-1-en-1-yl trifluoromethanesulfonates (1.08 g, 4.12 mmol, 1 equiv) prepared in Step C above, and N,N-dimethylformamide (50 mL) to yield a light yellow solution. The solution was briefly degassed by bubbling nitrogen gas through the solution for 5 minutes. To the solution was then added pinacol diborane (3.62 g, 14.2 mmol, 1.1 equiv), potassium acetate (3.82 g, 38.9 mmol, 3 equiv) and diphenylphosphinoferrocine palladium(II) chloride (237 mg, 0.32 mmol, 0.03 equiv) with additional degassing for 5 minutes. The reaction vessel was fitted with a reflux condenser and placed under nitrogen atmosphere. The reaction vessel was then placed in a preheated 80° C. heating mantle overnight for 6 hours. The resulting mixture was then cooled to room temperature and filtered through a bed of CELITE (2 cm high) in a Buchner funnel (3 cm diameter). The filter cake was rinsed with ethyl acetate (three 25-mL portions). The dark brown filtrate was cast into a separator funnel and diluted with water (50 mL). The aqueous phase was cut and extracted with ethyl acetate (three 25-mL portions). The combined organic phases were washed with water (five 20-mL) portions, dried over anhydrous magnesium sulfate, and gravity filtered. The filtrate was concentrated in vacuo to yield a mixture of 2',3',6',6'-[$D_4$]-deuterated and 2',5',6',6'-[$D_4$]-deuterated 2-(4,4-dimethylcyclohex-1-en-1-yl)-4,4,5,5-tetramethyl-1,3,2-dioxaborolanes as an oil (2.06 g, 66% yield).

Step E: Mixture of 2',3',6',6'-[$D_4$]-deuterated and 2',5',6',6'-[$D_4$]-deuterated n-Butyl 4-(5-amino-6-(4,4-dimethylcyclohex-1-en-1-yl)pyridin-2-yl)-2,6,6-trimethyltetrahydro-2H-pyran-2-carboxylates

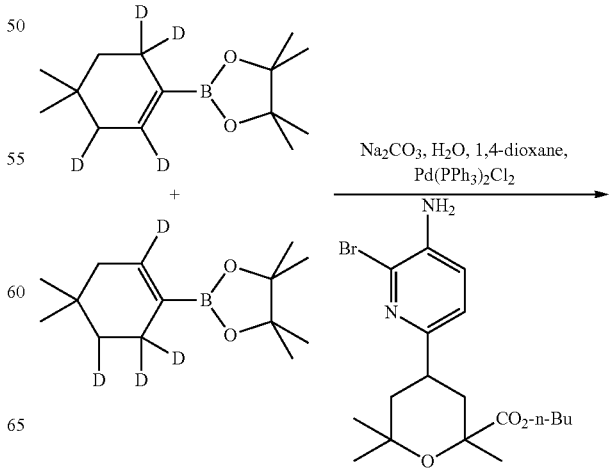

-continued

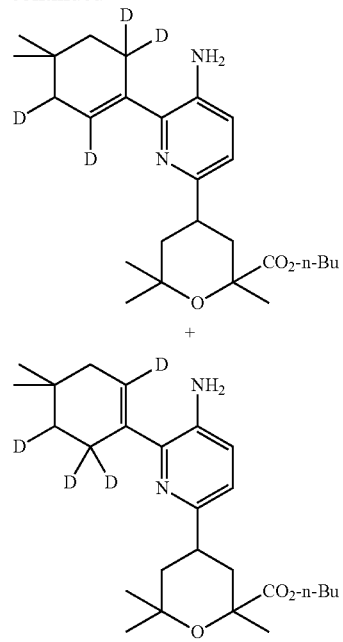

The title mixture of 2',3',6',6'-[D₄]-deuterated and 2',5',6',6'-[D₄]-deuterated n-Butyl 4-(5-amino-6-(4,4-dimethylcyclohex-1-en-1-yl)pyridin-2-yl)-2,6,6-trimethyltetrahydro-2H-pyran-2-carboxylates was prepared by reacting the mixture of a mixture of 2',3',6',6'-[D₄]-deuterated and 2',5',6',6'-[D₄]-deuterated 2-(4,4-dimethylcyclohex-1-en-1-yl)-4,4,5,5-tetramethyl-1,3,2-dioxaborolanes, prepared as in Step D above, according to the procedure as described in Example 1, Step J, above.

Step F: Mixture of 2',3',6',6'-[D₄]-deuterated and 2',5',6',6'-[D₄]-deuterated 4-cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1H-imidazole-2-carboxamide)

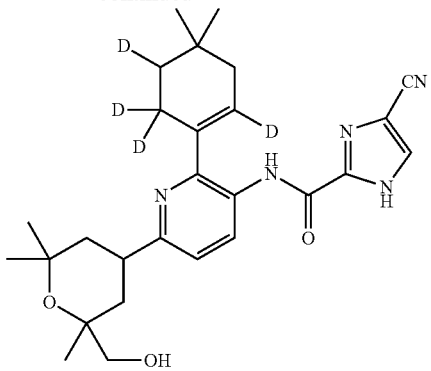

The mixture of 2',3',6',6'-[D₄]-deuterated and 2',5',6',6'-[D₄]-deuterated 4-cyano-N-(2-(4,4-dimethylcyclohex-1-en-1-yl)-6-(2-(hydroxymethyl)-2,6,6-trimethyltetrahydro-2H-pyran-4-yl)pyridin-3-yl)-1H-imidazole-2-carboxamides was prepared by reacting the mixture of 2',3',6',6'-[D₄]-deuterated and 2',5',6',6'-[D₄]-deuterated n-butyl 4-(5-amino-6-(4,4-dimethylcyclohex-1-en-1-yl)pyridin-2-yl)-2,6,6-trimethyltetrahydro-2H-pyran-2-carboxylates prepared as in Example 3, Step E above, according to the procedures as described in Example 1, Steps K, L and M, above (more particularly, reacting sequentially with (1) potassium salt of 4-cyano-1-(2-trimethylsilyl-ethoxymethyl)-1H-imidazole-2-carboxylic acid (0.75 g, 2.48 mmol); then with (2) DIBAL; and then with (3) TBAF, as described therein).

ESI-MS (M+1) 482. ¹H NMR: (CDCl₃, 400 MHz): δ (ppm) 11.7 (s, 1H), 9.22 (s, 1H), 8.60 (d, 1H), 7.70 (s, 1H), 7.20 (d, 1H), 3.50 (d, 1H), 3.40-3.30 (m, 2H), 2.55 (br), 2.15 (m), 2.02 (t), 1.90 (m), 1.30-1.50 (m, 4H), 1.40 (s, 3H), 1.35-1.25 (m, 6H), 1.12 (s, 6H).

Example 4: (Mixture of Compound of Formula (I-M2-D4a) and (I-M2-D4b)

Mixture of 2',3',6',6'-[D₄]-deuterated and 2',5',6',6'-[D₄]-deuterated 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylic acid

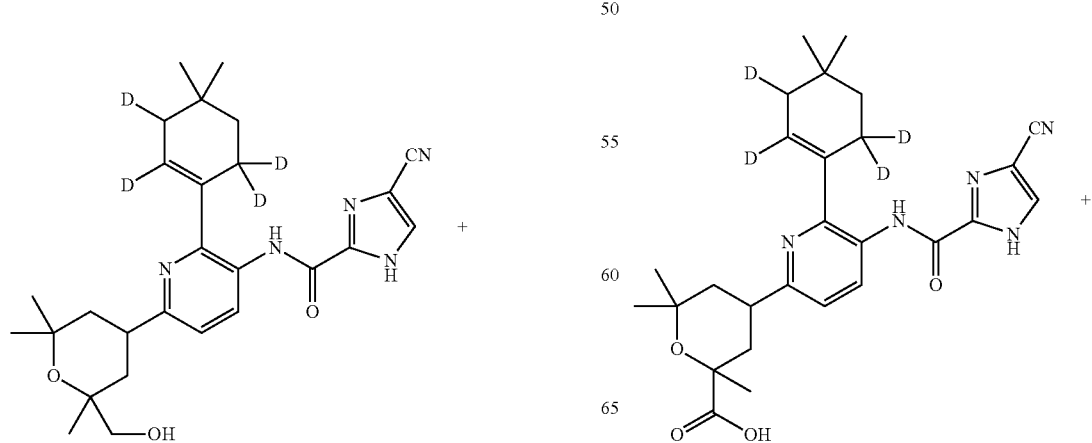

53

-continued

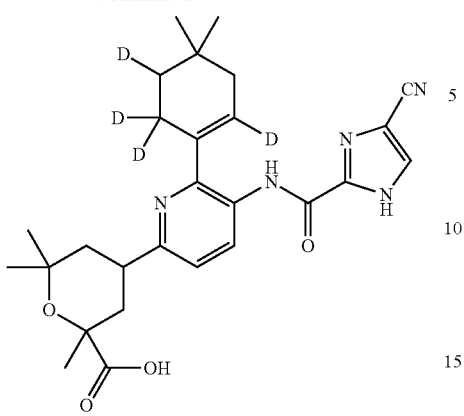

The mixture 2',3',6',6'-[D4]-deuterated and 2',5',6',6'-[D$_4$]-deuterated 4-(5-(4-cyano-1H-imidazole-2-carboxamido)-6-(4,4-dimethylcyclohex-1-en-1-yl)pyridin-2-yl)-2,6,6-trimethyltetrahydro-2H-pyran-2-carboxylic acid was similarly prepared, reacting the mixture of 2',3',6',6'-[D$_4$]-deuterated and 2',5',6',6'-[D$_4$]-deuterated n-butyl 4-(5-amino-6-(4,4-dimethylcyclohex-1-en-1-yl)pyridin-2-yl)-2,6,6-trimethyltetrahydro-2H-pyran-2-carboxylates, prepared as in Example 3, Step E above, according to the procedures as described in Example 2, above (more particularly, reacting sequentially with (1) TBAF; then with (2) LiOH; and then acidifying with aqueous HCl, as described therein).

MS m/z 496 (MH$^+$). $^1$H NMR: (CDCl$_3$, 400 MHz): δ (ppm) 11.5 (s, 1H), 9.70 (s, 1H), 8.65 (br, 1H), 7.75 (s, 1H), 7.12 (br, 1H), 3.35 (m, 1H), 2.65 (s), 2.25 (d), 2.15 (br), 2.05-1.82 (m), 1.80-1.20 (m, 9H), 1.15 (s, 6H).

Example 5: (Mixture of Compound of Formula (P-D4a) and (P-D4b))

Mixture of 2',3',6',6'-[D$_4$]-deuterated 4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamide and 2',5',6',6'-[D$_4$]-deuterated 4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamide

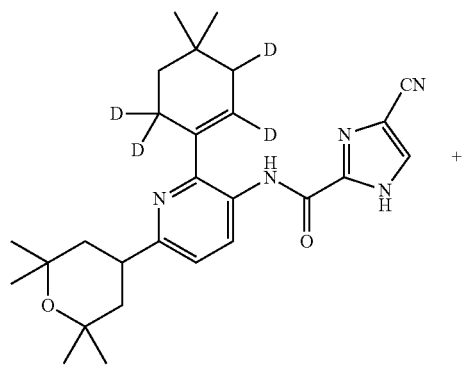

+

54

-continued

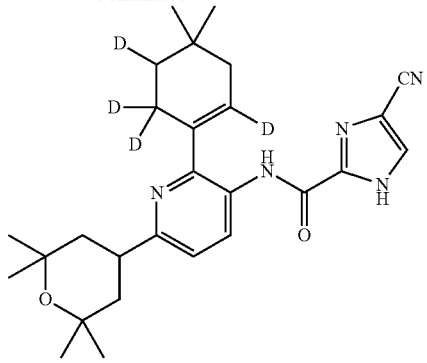

Step A: Mixture of 2',3',6',6'[D$_4$]-deuterated and 2',5',6',6'[D$_4$]-deuterated 2-(4,4-dimethyl-cyclohex-1-enyl)-6-(2,2,6,6-tetramethyl-tetrahydro-pyran-4-yl)-pyridin-3-ylamine

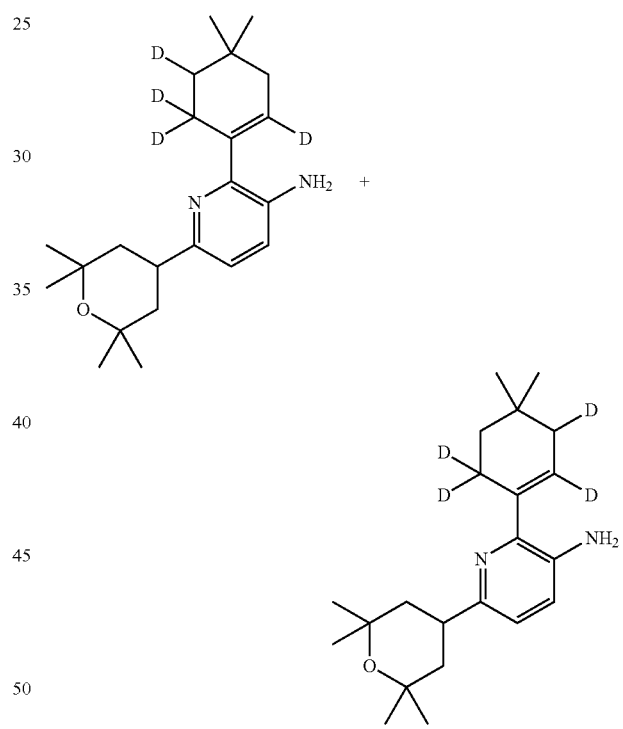

A mixture of 2',3',6',6'-[D$_4$]-deuterated and 2',5',6',6'-[D$_4$]-deuterated 2-(4,4-dimethylcyclohex-1-en-1-yl)-4,4,5,5-tetramethyl-1,3,2-dioxaborolanes (200 mg, 0.64 mmol) prepared for example as described in Example 3, STEP D, 2-bromo-6-(2,2,6,6-tetramethyl-tetrahydro-pyran-4-yl)-pyridin-3-ylamine (189 mg, 0.79 mmol), Pd(PPh$_3$)$_4$ (20 mg, 0.017 mmol), Na$_2$CO$_3$ (500 mg, 4.7 mmol), and LiCl (30 mg, 0.71 mmol) in DME/H$_2$O (1:1) (4 mL) was stirred at 80° C. under N$_2$ for 4 hours. The resulting mixture was cooled to room temperature and the organic phase purified by chromatography on a silica gel column with 0-10% gradient of ethyl acetate/heptanes to yield a white solid (181 mg), which contained a mixture of 2',3',6',6'-[D$_4$]-deuterated and 2',5',6',6'-[D$_4$]-deuterated 2-(4,4-dimethyl-cyclohex-1- enyl)-6-(2,2,6,6-tetramethyl-tetrahydro-pyran-4-yl)-pyridin-3-ylamine. MS m/z 347 (M+1).

Step B: Mixture of 2',3',6',6'-[D₄]-deuterated and 2',5',6',6'-[D₄]-deuterated 4-cyano-1-(2-trimethylsilanyl-ethoxymethyl)-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide

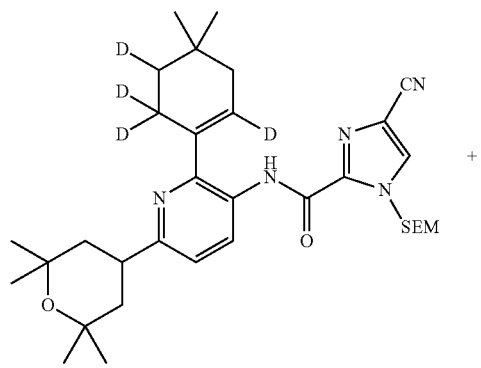

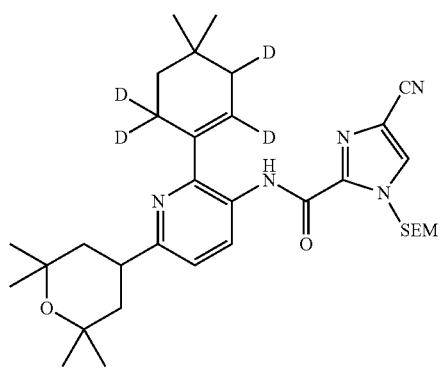

To a mixture of 2',3',6',6'-[D₄]-deuterated and 2',5',6',6'-[D₄]-deuterated 2-(4,4-dimethyl-cyclohex-1-enyl)-6-(2,2,6,6-tetramethyl-tetrahydro-pyran-4-yl)-pyridin-3-ylamines (243 mg, 0.70 mmol), potassium salt of 4-cyano-1-(2-trimethylsilanyl-ethoxymethyl)-1H-imidazole-2-carboxylic acid (300 mg, 0.98 mmol), and PyBrop (498 mg, 1.05 mmol) in dichloroethane (6 mL), was added diisopropylethylamine (0.244 mL, 1.4 mmol). The resulting mixture was stirred at room temperature for 4 hours and then quenched with saturated NaHCO₃ solution (2 mL). The organic layer was separated and aqueous layer was extracted with dichloromethane (2×2 mL). The organic phases were combined and concentrated in vacuo. The resulting residue was purified by chromatography on a silica gel column with 0-15% gradient of ethyl acetate/heptanes to yield a white solid (382 mg), which contained a mixture of 2',3',6',6'-[D₄]-deuterated and 2',5',6',6'-[D₄]-deuterated 4-cyano-1-(2-trimethylsilanyl-ethoxymethyl)-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide. MS m/z 596 (M+1).

Step C: Mixture of 2',3',6',6'-[D₄]-deuterated and 2',5',6',6'-[D₄]-deuterated 4-cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide

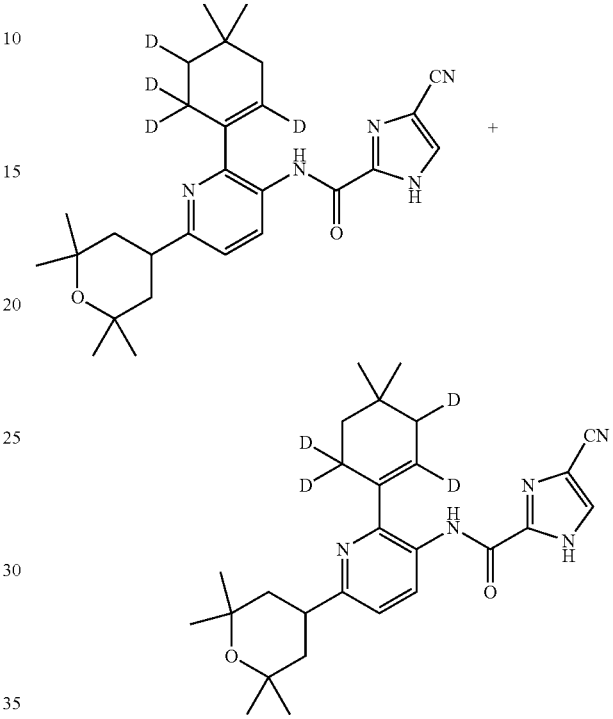

To a solution of 2',3',6',6'-[D₄]-deuterated and 2',5',6',6'-[D₄]-deuterated 4-cyano-1-(2-trimethylsilanyl-ethoxymethyl)-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide (208 mg, 0.35 mmol) in THF (10 mL), was added a 1M THF solution of TBAF (0.4 mL). The resulting solution was stirred at 70° C. overnight and then concentrated. The resulting residue was purified by chromatography on a silica gel column with 0-50% gradient of ethyl acetate/heptanes to yield a white solid (115 mg), which contained a mixture of 2',3',6',6'-[D₄]-deuterated and 2',5',6',6'-[D₄]-deuterated 4-cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide.

$^1$H NMR: (CD₃OD, 300 MHz): δ (ppm) 8.55 (d, 1H), 8.00 (s, 1H), 7.25 (d, 1H), 3.30 (m, 1H, overlap with solvent), 2.08 (m), 1.82 (m), 1.60 (m, 4H), 1.38 (s, 6H), 1.25 (s, 6H), 1.10 (s, 6H); MS m/z 466 (M+1).

Example 6

Separation of Diastereomers of the Compound of Formula (I-M2) and the Compound of Formula (I-M7)

The compound of formula (I-M2), prepared as described herein, was separated by supercritical fluid chromatography (SFC) on a Daicel Chiralpak ID column using CO₂/isopropanol/0.2% isopropylamine, to yield the compound of formula (I-M2-2S,4R) and the compound of formula (I-M2-

2R,4S), each with a predicted diastereomeric excess of greater than or equal to about 95%.

The measured chiral HPLC purity for the two isolated diastereomers of the compound of formula (I-M2) was 97%.

The compound of formula (I-M7), prepared as described herein, was separated by supercritical fluid chromatography (SFC) on a Daicel Chiralpak ID column using $CO_2$/isopropanol/0.2% isopropylamine, to yield the compound of formula (I-M7-2S,4R) and the compound of formula (I-M7-2R,4S), each with a predicted diastereomeric excess of greater than or equal to about 95%.

The measured chiral HPLC purity for the two isolated diastereomers of the compound of formula (I-M7) was 100%.

Biological Example 1

Human c-Fms Protein Kinase Assay ($\gamma$-$^{33}$P-ATP Format)

c-fms(h) was incubated with 8 mM MOPS pH 7.0, 0.2 mM EDTA, 250 μM KKKSPGEYVNIEFG, 10 mM MgAcetate and [γ-33P-ATP] (specific activity approx. 500 cpm/pmol, concentration as required). The reaction was initiated by the addition of the MgATP mix. After incubation for 40 minutes at room temperature, the reaction was stopped by the addition of 3% phosphoric acid solution. 10 μL of the reaction was then spotted onto a P30 filtermat and washed three times for 5 minutes in 75 mM phosphoric acid and once in methanol prior to drying and scintillation counting.

Representative compounds of formula (I) of the present invention were tested according to the procedure as described in Biological Example 1 above, with results as listed in Table 1 below.

TABLE 1

| Compound | $IC_{50}$ |
|---|---|
| (I-M2) | 11 nM |
| (I-M7) | 10 nM |
| (P) | 18 nM |

Biological Example 2

Inhibition of CSF-1 Induced Monocyte MCP-1 Expression Cell Based Assay

Representative compounds of the present invention were additionally tested in an in vitro assay measuring inhibition of CSF-1 induced monocyte MCP-1 expression, as described briefly below.

Human monocytes were isolated from the blood of three donors by negative selection using RosetteSep® human monocyte enrichment cocktail from StemCell Technologies (Cat. #15068). Monocytes ($1\times10^5$/well) were cultured in 96 well polypropylene plates (Corning 3790) with Roswell Park Memorial Institute (RPMI) 1640 media containing 10% heat-inactivated fetal bovine serum and 1% Penicillin-Streptomycin, Liquid (complete media). Cultures were adjusted to contain graded concentrations (0.33 to 0.000151 micromolar or zero micromolar) of test compound and 10 ng/mL human CSF-1. Conditioned media were harvest after approximately eighteen hours of culture and assayed for MCP-1 protein using a specific ELISA.

Representative compounds of the present invention were tested according to the procedure as described in Biological example 2, above, with determined $IC_{50}$ values as listed in Table 2, below.

TABLE 2

Inhibition of CSF-1 Induced Monocyte MCP-1 Expression

| Compound | $IC_{50}$ (mM) (Mean (n = 3) ± Std. Dev) |
|---|---|
| (I-M2-2S,4R) | 0.00293 ± 0.00155 |
| (I-M2-2R,4S) | 0.00847 ± 0.00341 |
| (I-M7-2S,4R) | 0.00100 ± 0.00055 |
| (I-M7-2R,4S) | 0.00237 ± 0.00046 |
| (P) | 0.00125 ± 0.00085 |

Biological Example 3

Human, Dog and Rat c-Fms Enzyme Assay (Fluorescence Immunoassay Format)

Materials:

Human c-fms protein (N-terminal 6His-tagged, amino acids 538-972), dog c-fms protein (N-terminal 6His-tagged, amino acids 535-967) and rat c-fms protein (N-terminal 6His-tagged, amino acids 536-978) were purified in-house using a HisTrap column. The Antibody Beacon tyrosine kinase assay kit was purchased from Life Technologies. The c-fms peptide substrate, SYEGNSYTFIDPTQ, and the phosphorylated product, SYEGNSpYTFIDPTQ, were obtained from American Peptide Company. Non-binding surface (NBS) 384-well plates were obtained from Corning.

c-Fms Enzyme Assay Procedure:

In this assay, recombinant human, dog or rat c-fms catalyzed the phosphorylation of the FMS peptide substrate, SYEGNSYTFIDPTQ, with the phosphorylated product detected by a fluorescence immunoassay. The c-fms assay buffer consisted of 25 mM HEPES, pH 7.0, 5 mM $MgCl_2$, 1 mM DTT and 0.01% Brj-35. 5 μl of 3× of the test compound(s) in assay buffer containing 1% DMSO were added to the wells of a 384-well NBS plate, at concentrations of 1 μM down to 0.00002 μM (applying a 1:3 dilution scheme). c-fms activity was assayed in the presence of 300 μM SYEGNSYTFIDPTQ, 1 mM ATP and human, dog or rat c-fms in a total volume of 15 μl. The reaction was initiated with ATP. The assay plates were sealed with aluminum sealing tape and incubated at room temperature for 2 h. At the end of the incubation, 5 μl of 4× detection reagent were added to each well (Antibody Beacon tyrosine kinase assay kit; the 4× detection reagent consisted of 100 nM Oregon Green 488 ligand and 200 nM anti-phosphotyrosine antibody and was prepared just prior to use). The plates were centrifuged at 1000×g for 1 min. Fluorescence was measured after 10 min on a Safire II reader at excitation/emission of 492/517 nm. RFU values were converted to micromolar phosphopeptide using a SYEGNSpYTFIDPTQ standard curve. $IC_{50}$ values were calculated using GraphPad Prism 5.

Representative compounds of formula (I) of the present invention were tested according to the procedure as described in Biological Example 3 above, with results as listed in Table 3 below. For the human FMS results, the results presented below are an average of n=3.

TABLE 3

| | Human, Dog and Rat c-fms Assay Results | | |
|---|---|---|---|
| Compound | Human IC$_{50}$ (µM) | Dog IC$_{50}$ (µM) | Rat IC$_{50}$ (µM) |
| (I-M2-2S,4R) | 0.0022 | 0.0020 | 0.0022 |
| (I-M2-2R,4S) | 0.0018 | 0.0020 | 0.0025 |
| (I-M7-2S,4R) | 0.0079 | 0.0066 | 0.0079 |
| (I-M7-2R,4S) | 0.0071 | 0.0080 | 0.0096 |
| (P) | 0.010 | 0.016 | 0.011 |

Formulation Example 1 (Prophetic Example): Oral Formulation

As a specific embodiment of an oral composition, 100 mg of the Compound of formula (I-M2) prepared as in Example 1 is formulated with sufficient finely divided lactose to provide a total amount of 580 to 590 mg to fill a size 0 hard gel capsule.

Formulation Example 2 (Prophetic Example): Oral Formulation

As a specific embodiment of an oral composition, 100 mg of the Compound of formula (I-M7) prepared as in Example 2 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A mixture of a compound of formula (I-M2-D4a)

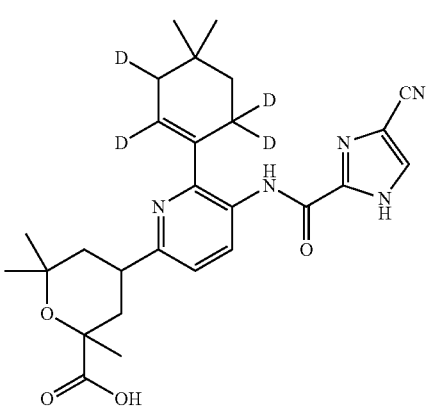

and a compound of formula (I-M2-D4b)

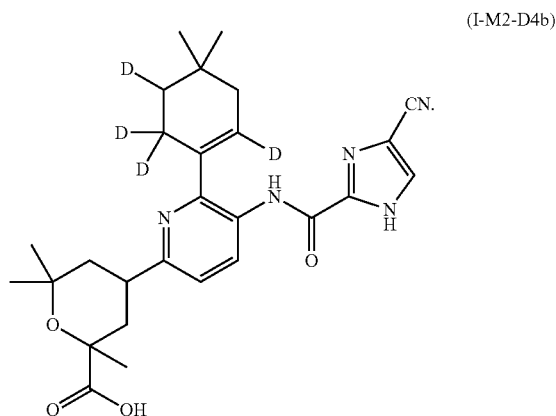 [SMILES: [2H]C1=C(c2nc(C3CC(C)(C)OC(C)(C(=O)O)C3)ccc2NC(=O)c2nc(C#N)c[nH]2)C([2H])([2H])C([2H])C(C)(C)C1]

2. A mixture of a compound of formula (I-M7-D4a)

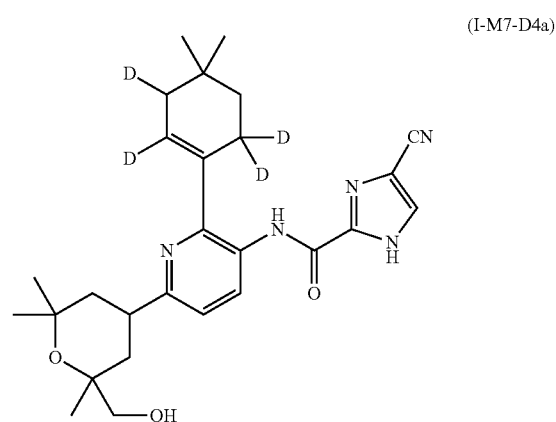 [SMILES: [2H]C1=C(c2nc(C3CC(C)(C)OC(C)(CO)C3)ccc2NC(=O)c2nc(C#N)c[nH]2)C([2H])([2H])CC(C)(C)C1[2H]]

and a compound of formula (I-M7-D4b)

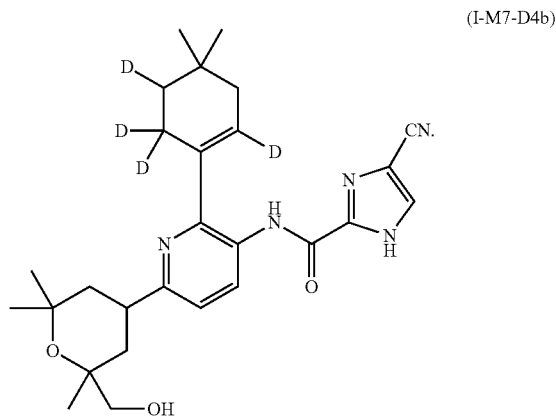 [SMILES: [2H]C1=C(c2nc(C3CC(C)(C)OC(C)(CO)C3)ccc2NC(=O)c2nc(C#N)c[nH]2)C([2H])([2H])C([2H])C(C)(C)C1]

3. A mixture of a compound of formula (P-D4a) and a compound of formula (P-D4b)
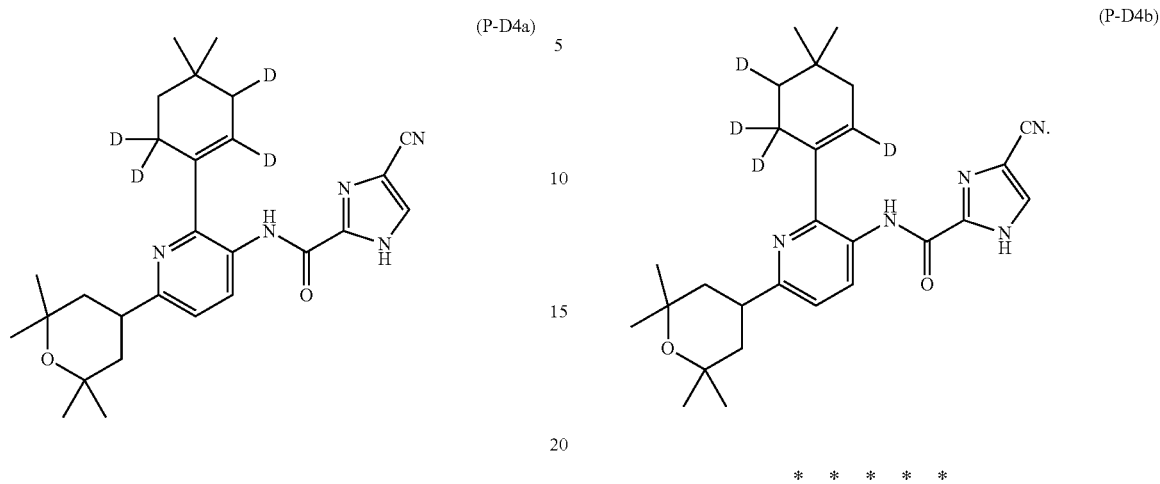
* * * * *